US009776948B2

(12) United States Patent
Smidt et al.

(10) Patent No.: US 9,776,948 B2
(45) Date of Patent: Oct. 3, 2017

(54) PROCESS FOR THE PREPARATION OF SUCCINIC ACID ESTER

(71) Applicant: Johnson Matthey Davy Technologies Limited, London (GB)

(72) Inventors: Martin Lucas Smidt, London (GB); Ian Campbell, London (GB); Graham Reed, London (GB); Paul Gordon, Durham (GB); Christopher Ferguson, Durham (GB)

(73) Assignee: Johnson Matthey Davy Technologies Limited, London (GB)

( * ) Notice: Subject to any disclaimer, the term of this patent is extended or adjusted under 35 U.S.C. 154(b) by 37 days.

(21) Appl. No.: 14/785,794

(22) PCT Filed: Dec. 2, 2014

(86) PCT No.: PCT/GB2014/053589
§ 371 (c)(1),
(2) Date: Oct. 20, 2015

(87) PCT Pub. No.: WO2015/082916
PCT Pub. Date: Jun. 11, 2015

(65) Prior Publication Data
US 2016/0272568 A1 Sep. 22, 2016

(30) Foreign Application Priority Data

Dec. 6, 2013 (GB) .................................. 1321611.4

(51) Int. Cl.
C07C 67/30 (2006.01)
C07C 67/08 (2006.01)
B01D 3/00 (2006.01)

(52) U.S. Cl.
CPC .............. *C07C 67/08* (2013.01); *B01D 3/009* (2013.01)

(58) Field of Classification Search
None
See application file for complete search history.

(56) References Cited

U.S. PATENT DOCUMENTS

| | | | |
|---|---|---|---|
| 3,830,830 A | 8/1974 | Cleveland et al. |
| 4,584,419 A | 4/1986 | Sharif et al. |
| 4,656,297 A | 4/1987 | Kouba et al. |
| 4,751,334 A | 6/1988 | Turner et al. |
| 4,767,869 A | 8/1988 | Harrison et al. |
| 4,794,824 A | 1/1989 | Chapman |
| 4,795,824 A | 1/1989 | Kippax et al. |
| 4,919,765 A | 4/1990 | Wilkes et al. |
| 4,945,173 A | 7/1990 | Wood |
| 5,254,758 A | 10/1993 | Hiles et al. |
| 5,310,954 A | 5/1994 | Hiles et al. |
| 5,723,639 A | 3/1998 | Datta et al. |
| 5,958,744 A | 9/1999 | Berglund et al. |
| 6,265,790 B1 | 7/2001 | Vogman |
| 8,246,792 B2 | 8/2012 | Fruchey et al. |
| 2006/0252956 A1 | 11/2006 | Miller et al. |
| 2013/0303796 A1 | 11/2013 | Hwang et al. |

FOREIGN PATENT DOCUMENTS

| | | |
|---|---|---|
| CN | 101323566 | 12/2008 |
| CN | 103342638 | 10/2013 |
| EP | 1849764 | 10/2007 |
| JP | 01-1216958 | 8/1989 |
| JP | 04-091055 | 3/1992 |
| WO | 86/03189 | 6/1986 |
| WO | 88/00937 | 2/1988 |
| WO | 90/08127 | 7/1990 |
| WO | 91/01960 | 2/1991 |
| WO | 99/35113 | 7/1999 |
| WO | 99/35136 | 7/1999 |

OTHER PUBLICATIONS

"Reaction Kinetics for the Heterogeneously Catalyzed Esterification of Succinic Acid with Ethanol" Kolah A K et al Ind. Eng. Chem. Res., 2008, 47(15) pp. 5313-5317.
"Pervaporation-assisted Esterification of Lactic and Succinic Acids with Downstream Ester Recovery" Benedict et al, J. Membrane Sci., 2006, 281 pp. 535-445.
"Combined Technology of Catalytic Esterification and Absorption of Succinic Acid" Ding B et al The Chinese Journal of Process Engineering, pp. 100-104, Feb. 20, 2007 (Abstract Only).
"Preparation of Diethyl Succinate by Catalytic Esterification and Absorption Dehydration" Gong C et al China Surfactant Detergent Cosmetics, pp. 245-248, Apr. 2008 (Abstract Only).
"Purification of succinic acid from synthetic solution using vapor permeation-assisted esterification coupled with reactive distillation", A Boontawan, Advanced Materials Research, vols. 550-553, pp. 3008-3011, Jul. 2012.

(Continued)

Primary Examiner — Sudhakar Katakam
Assistant Examiner — Ana Z Muresan
(74) Attorney, Agent, or Firm — Armstrong Teasdale LLP

(57) ABSTRACT

A process for production of dialkyl succinate from bio-succinic acid feedstock where solid bio-succinic acid is fed to a reactor to react with alkanol by autocatalytic esterification. Products from the reactor including unreacted succinic acid, mono alkyl ester, dialkyl ester, alkanol, water and impurities are sent to a reaction distillation column for esterification of succinic acid and further esterification of mono alkyl ester with upflowing alkanol. The bottoms products from the reaction distillation column including residual succinic acid, mono alkyl ester, dialkyl ester, impurities and alkanol are sent to a bottoms stream separation zone where di-alkyl ester is separated from alkanol, succinic acid, mono alkyl ester and impurities. The tops products from the reaction distillation column including alkanol, water and organic components are sent to a top stream distillation zone where alkanol is separated from water and organic components. The organic components are recycled to the reaction zone column.

28 Claims, 5 Drawing Sheets

(56) References Cited

OTHER PUBLICATIONS

"Diethyl succinate synthesis by reactive distillation", pp. 151-162, ISSN: 1383-5866, Separation and Purification Technology, vol. 88, 2012, (Orjuela, Alvaro et al).
"A novel process for recovery of fermentation-derived succinic acid", pp. 31-37, ISSN: 1383-5866, Separation and Purification Technology, vol. 83, 2012, (Orjuela, Alvaro et al).
"Mixed Succinic Acid/Acetic Acid Esterification with Ethanol by Reactive Distillation", pp. 9209-9220, ISSN: 0888-5885, Industrial & Engineering Chemistry Research, vol. 50 (15), 2011, (Orjuela, Alvaro et al).
Towards a Bio-based Industry: Benign Catalytic Esterifications of Succinic Acid in the Presence of Water, Budarin et al vol. 13, Issue 24, pp. 6914-6919, Aug. 17, 2007.
Feasibility of Production Methods for Succinic Acid Derivatives; a Marriage of Renewable Resources and Chemical Technology; A Cukalovic et al Biofuels, Bioproducts and Biorefining vol. 2, issue 6, pp. 505-529, Nov./Dec. 2008.
Chemical Transformations of Succinic Acid Recovered from Fermentation Broths by a Novel Direct Vacuum Distillation—Crystallisation Method, R Lugue et al, Green Clem., 2009, 11, 193-200.
International Preliminary Report on Patentability for PCT/GB2014/053589 issued Jun. 7, 2016. 7 pages.

PROCESS FOR THE PREPARATION OF SUCCINIC ACID ESTER

The present invention relates to a process for the production of 1,4-butanediol, optionally with its co-products tetrahydrofuran and/or γ-butyrolactone from a feedstock comprising succinic acid produced by a fermentation based process It is known to produce diols by reaction of dicarboxylic acids and/or anhydrides, or mono or di-alkyl esters, lactones, and mixtures thereof with hydrogen. Commercially, where the desired product is 1,4-butanediol, typically with the co-products tetrahydrofuran and γ-butyrolactone, the starting material is normally a dialkyl ester of maleic acid and/or anhydride, such as dimethyl maleate or diethyl maleate, which may contain minor amounts of dialkyl fumarate and/or dialkyl succinate.

Information relating to these processes can be found in, for example, U.S. Pat. No. 4,584,419, U.S. Pat. No. 4,751,334, WO86/03189, WO88/00937, U.S. Pat. No. 4,767,869, U.S. Pat. No. 4,945,173, U.S. Pat. No. 4,919,765, U.S. Pat. No. 5,254,758, U.S. Pat. No. 5,310,954 and WO91/01960.

The dialkyl maleates which are used as feedstock in these conventional reaction processes may be produced by any suitable means. The production of dialkyl maleates for use in such processes is discussed in detail in U.S. Pat. No. 4,584,419, U.S. Pat. No. 4,751,334, WO88/00937, U.S. Pat. No. 4,795,824 and WO90/08127.

In one conventional process for the production of 1,4-butanediol and co-product tetrahydrofuran with optional production of γ-butyrolactone, a dialkyl ester, such as dimethyl maleate together with any residual methanol from the esterification reactor, is fed to a vaporiser where it is vaporised by a stream of hot cycle gas fed to the vaporiser which may be mixed with make-up hydrogen. The cycle gas will normally contain a high concentration of hydrogen gas but may also include other gases including hydrocarbons, carbon oxides, methane and nitrogen. Further, where the cycle gas includes recycled gases from downstream, condensables including product ether, methanol, water, co-products and by-products may also be present.

The combined vaporous stream from the vaporiser is then passed to a reactor where it is reacted in the presence of a catalyst to form 1,4-butanediol, tetrahydrofuran and/or γ-butyrolactone. The product stream is cooled and the reaction products are condensed and separated from the excess cycle gas before being passed into a refining zone. In the refining zone the various products are separated and the 1,4-butanediol and the tetrahydrofuran are removed. The γ-butyrolactone, together with the intermediate, dimethyl succinate, and some 1,4-butanediol may be recycled. In one arrangement the γ-butyrolactone may be at least partially extracted in an optional refining zone and recovered. The methanol water stream separated from the product mix will be recycled upstream. In general, a significant portion of the 1,4-butanediol produced by this or other conventional methods is subsequently converted to tetrahydrofuran.

The overall reaction which occurs is a series of steps and includes a final dehydration step in which the tetrahydrofuran is produced. A probable reaction path is set out in Scheme 1.

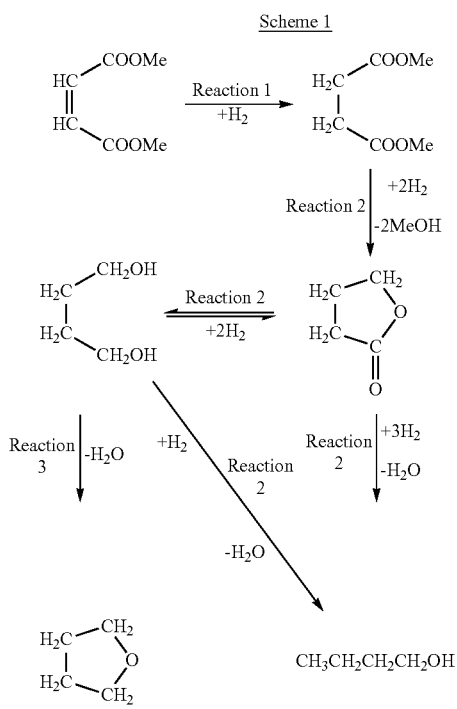

Scheme 1

An alternative process is described in WO99/35113 in which maleic anhydride esters are fed to a reaction process in which three different catalysts are used. First the maleate is converted to the succinate in the presence of the first catalyst which is a heterogeneous selective hydrogenation catalyst at a temperature of from 120° C. to 170° C. and a pressure of 3 to 40 bara. The succinate is then passed directly to the presence of the second catalyst where it is converted mainly into γ-butyrolactone. The product of the reaction with the second catalyst is then fed directly to the presence of a third catalyst which is used to dehydrate the γ-butyrolactone to produce tetrahydrofuran. Some of the γ-butyrolactone formed in the presence of the second catalyst is transferred to a second reaction loop operating at a higher pressure where it is converted to 1,4-butanediol.

As the first step in Scheme 1 and the first catalyst used in the alternative process described in WO99/35113 relates to the hydrogenation of the dimethyl maleate to dimethyl succinate, it has been suggested that dimethyl succinate or diethyl succinate may be suitable starting materials for the reaction with hydrogen to form 1,4-butanediol, tetrahydrofuran and/or γ-butyrolactone.

One process in which dimethyl succinate is used in the production of tetrahydrofuran and 1-4-butanediol is described in U.S. Pat. No. 4,656,297. In this process, methanol is added to the ester feed to increase conversion and reduce transesterification. Another example of a process in which dimethyl succinate is suggested as a feed is WO99/35136 in which reaction with hydrogen occurs over two different catalysts, to form a mixture of tetrahydrofuran and γ-butyrolactone.

Maleic anhydride is commonly produced commercially from benzene or n-butane, both of which are ultimately derived from crude oil. It is therefore desirable to look for alternative starting materials which are not derived from oil in an attempt to improve the environmental impact and potentially improve the economics.

Recently, there have been significant advancements in processes to produce and recover succinic acid from the fermentation of sugars. Examples of processes can be found in, for example, U.S. Pat. No. 5,958,744, U.S. Pat. No. 6,265,190 and U.S. Pat. No. 8,246,792. Currently demonstration plants have been constructed. It is anticipated that in due course such processes may be able to compete with maleic anhydride as an economic feedstock for the production of 1,4-butanediol.

Where succinic acid is used as the feedstock, it will generally first be esterified to produce dialkyl succinate. While the processes and plant described in U.S. Pat. No. 4,795,824 and WO90/08127 may be used to produce dialkyl succinates from succinic acid, there are various disadvantages and drawbacks.

The processes described in these prior art systems are not ideally suited to being carried out where the starting material is succinic acid. This is particularly the case where the succinic acid is produced by a fermentation process. For ease of reference, we will refer to succinic acid produced by fermentation processes as "bio-succinic acid" and the term should be construed accordingly.

Bio-succinic acid generally contains impurities. These may be fermentation residues and by-products. These impurities which may include sulphur, may be detrimental to the operation of catalysts used in reactions which utilise this bio-succinic acid. This is particularly problematic where the subsequent reactions utilise a copper based catalyst. Another arrangement where the impurities are particularly detrimental is where the subsequent reaction uses an acid resin catalyst such as an esterification. Whilst it may be possible to address the problem by removal of these impurities by purification processes prior to contact with catalyst in the subsequent reactions, the number of steps required to produce succinic acid of sufficient purity are substantial. The requirement for these purification steps significantly increase both the capital and operating costs associated with the succinic acid production plant.

It is therefore desirable to provide a process for the production of dialkly succinate from bio-succinic acid without the need for the complex and expensive purification steps.

JP1216958 describes a process for the esterification of succinic acid using a homogeneous acid catalyst. In this process, an extremely dilute solution of the succinic acid in methanol is supplied, with a homogeneous catalyst to the upper region of a distillation column where it is passed in counter-current to methanol added at the base of the column. Esterification occurs within the column and the dialkyl succinate is removed from the base of the column. As a very dilute solution of the succinic acid is used, about 1 to 20 wt percent, a large methanol recycle flow will be required and substantial costs will be incurred in separating the methanol from the water of esterification produced in the reaction. Example 1 of JP 1216958 illustrated the problems associated with the deactivation of a resin catalyst where the succinic acid is bio-succinic acid.

The problems associated with using bio-succinic acid in an esterification reaction in the presence of a resin catalyst are also illustrated in Example 1 of "Reaction Kinetics for the Heterogeneously Catalyzed Esterification of Succinic Acid with Ethanol" Kolah A K et al Ind. Eng. Chem. Res., 2008, 47(15) pp 5313-5317, "Pervaporation-assisted Esterification of Lactic and Succinic Acids with Downstream Ester Recovery" Benedict et al, J. Membrane Sci., 2006, 281 pp 435-445, "Combined Technology of Catalytic Esterification and Absorption of Succinic Acid" Ding B et al The Chinese Journal of Process Engineering 2007-01, U.S. Pat. No. 5,723,639, and "Preparation of Diethyl Succinate by Catalytic Esterification and Absorption Dehydration" Gang C et al China Surfactant Detergent & Cosmetics 2008-04.

Various processes have been suggested for carrying out the esterification in a non-catalysed system. However, these systems are likely to have a low conversion rate and will therefore have a high acid content. Since many of the known processes for producing, for example, 1,4-butanediol use a copper based catalyst, the presence of the acid is problematic since it will be deactivated by the acidic species present. This will necessitate regular shut down to replace the deactivated catalyst. To address this, the acid would have to be removed, which would require a number of steps which would add to the capital and operating costs of the process.

Using dialkyl succinate may overcome the problems associated with the high heat released on the conversion of the double bond and offer various other advantages such as obviating the risks of fumarates being formed which is also a problem associated with using maleic anhydride as a starting material. However, if the di-esterification of the succinic acid is not complete, acidic species will still be present in the reaction feed which can lead to deactivation of the catalyst unless steps are taken to remove the acid. It is therefore desirable to have a process which produces complete conversion to the di-ester and in particular a di-ester which is a suitable feed to a hydrogenation reaction. High conversion will require a large excess of dry alkanol. The recovery and recycle of this dry alkanol incurs high capital and operating costs.

There are also problems associated with using succinic acid as the starting material. Succinic acid is a crystalline solid at ambient temperatures and has a melting point above normal esterification temperatures. In addition it has low solubility in water and methanol. These limit the manner in which it can be used. This presents challenges in using succinic acid as a starting material in conventional esterification processes which are generally tailored to liquid feeds. Even if the succinic acid is provided in solution, this can be problematic since generally it will be provided as an aqueous solution which increases the water load on the system and may retard the esterification reaction since the presence of water will generally move the equilibrium of the reaction toward the acid rather the desired ester.

A further problem is that the volatility of the dialkyl succinate means that although the diester is predominately removed from the base of the column in the counter-current reaction, between the acid and the alkanol, a portion will carry over from the top of the reaction column and will be lost thereby impacting on the economics of the process.

It is therefore desirable to provide a process which addresses at least some of the above-identified problems starting with a bio-succinic acid. It is particularly desirable to provide a process which addresses all of the above problems.

The problem may be addressed by carrying out an autocatalytic reaction in a reactor, which will generally be a stirred tank reactor, before passing the partially esterified succinate to a counter-current esterification reaction column and then carrying out separation and recycling unreacted acid and mono-ester to the reaction column and purging the impurities.

Thus according to the present invention, there is provided a process for the production of dialkyl succinate from a bio-succinic acid feedstock comprising the steps of:

(a) feeding bio-succinic acid to a first reactor where it is contacted with alkanol, said first reactor being operated at a suitable temperature and pressure to enable autocatalytic esterification to occur;
(b) passing a stream removed from the first reactor comprising unreacted succinic acid, mono alkyl ester, dialkyl ester, alkanol, water and any impurities to a point at or near the top of a reaction zone column operated at temperatures and pressures to enable esterification of the succinic acid and further esterification of the mono alkyl ester, and passing said stream in counter-current reaction to upflowing additional alkanol;
(c) removing a stream from at or near the bottom of the reaction zone column comprising components selected from residual succinic acid, monoalkyl ester, dialkyl ester, impurities and alkanol and passing said stream to a bottoms stream separation zone where said di-alkyl ester is separated from alkanol, and from the succinic acid, mono alkyl ester and impurities;
(d) recycling the succinic acid and mono alkyl ester to the reaction zone column;
(e) removing at least some of the impurities as a purge; and
(f) removing a stream comprising alkanol, water and organic components from at or near the top of the reaction zone column and passing said stream to a top stream distillation zone where the alkanol is separated, from the water and from the organic components and recycling the organic components to the reaction zone column.

The feed to the first reactor will comprise bio-succinic acid which will include the impurities which are present following the formation of the succinic acid by fermentation of biomass. The specific impurities present will depend on the source of the biomass and the specific fermentation process employed. For example, they will depend on the organism and operating conditions used, whether nutrients are added and if so which, and whether the fermentation is aerobic or anaerobic. However, they will generally include one or more of proteins, sugars, amino acids, succinamic acid, succinamides, ammonium, sulphur, chlorides, phosphorous, organics and metal ions. Organics include other organic acids such as acetic acid, pyruvic acid, fumaric acid, acrylic acid, malic acid and/or lactic acid. The metal ions may be present in the biomass due to nutrient or feed impurities. The present invention enables the reaction to be carried out without the requirement to separate out these impurities before reaction commences.

In one arrangement, the bio-succinic acid may be provided to the first reactor as a solid. In another arrangement, it may be provided as a slurry or solution in water or an alkanol.

The present invention may be operated with bio-succinic acid feed comprising 50 wt % or more succinic acid such as 60 wt % or 70 wt %. In one arrangement, the bio-succinic acid may comprise 80 wt % or more succinic acid.

Where the bio-succinic acid is provided as a solid or a slurry or solution in alkanol, it may include up to about 20 wt % water. However, a lower water content is generally preferred. The water content will vary with the crystallisation conditions and drying profile. In one arrangement, the typical water content will be in the region of about 5 wt % water. The remainder will generally be the impurities. Where the bio-succinic acid is in an aqueous solution, it will be understood that the water content will be higher.

The bio-succinic acid feed may be co-fed with one or more of maleic acid, maleic anhydride and mono-alkyl maleate. The bio-succinic acid may be additionally or alternatively co-fed with a stream containing succinic acid, succinic acid esters, water and alkanol or mixtures of these which are generated from other processes outside of the present invention such as recycle streams from down-stream processes such as purification as well as upstream processes such as succinic acid purification.

The first reactor may be a stirred tank reactor and is preferably a continuous stirred tank reactor.

Any suitable reaction conditions may be operated. In one arrangement the first reactor will be operated at a temperature in the region of from about 120° C. to about 140° C. This is particularly advantageous when solid bio-succinic acid is used as it will enable the crystals of succinic acid to be dissolved and to allow the esterification reaction to occur. Suitable temperatures include 120° C., 125° C., 130° C., 135° C. and 140° C. The pressure within the first reactor may be in the region of from about 5 bara to about 10 bara. This is the optimum pressure to keep the alkanol in solution. Suitable pressures include 5 bara, 6 bara, 7 bara, 8 bara, 9 bara and 10 bara. Where an elevated pressure is used, the first reactor will be operated at a sufficiently high temperature for the autocatalytic esterification reaction to proceed relatively fast, generally in the order of 20 to 90 minutes, and the vaporisation of the alkanol to be prevented. In one arrangement, vaporisation may be undesirable as it may adversely affect the reaction equilibrium. However, in some arrangements, some vaporisation may be allowed.

In one arrangement, the reaction time will be of the order of 40 to 50 minutes.

Any suitable ratio of alkanol to succinic acid may be selected for the first reactor. In one arrangement, the molar ratio selected will be of from about 1:1 to about 6:1 alkanol to succinic acid. Molar ratios of about 2:1, 3:1 and 4:1 may also be used. It will be understood that increased alkanol will reduce reaction time. However, the presence of increased alkanol will increase the cost of alkanol recycle.

Heat may be generated in the autocatalytic reaction in the first reactor. A portion of this may be used to overcome the heat of dissolution of the bio-succinic acid where the feed is a solid or slurry. Any residual heat may be recovered and utilised in the process or in upstream or downstream reactions. This may be by means of condensing vapourised alkanol or by alternative means. In an alternative arrangement, heat may have to be supplied to overcome the heat of dissolution.

The stream removed from the first reactor may be a solution but may contain some residual solids. In one arrangement, the stream removed from the first reactor may be a slurry.

The product stream from the first reactor comprising unreacted succinic acid, mono alkyl ester, dialkyl ester, alkanol, water and impurities may optionally be passed via a subsequent reaction vessel to increase the conversion of any mono-ester to the di-ester. Any suitable subsequent reaction vessel may be used. In one arrangement, a plug flow reaction vessel may be used. Any suitable reaction conditions may be used in this reactor which allows the further esterification to occur.

If the subsequent reaction vessel is used, the reaction stream is then passed to the reaction zone column. Where a subsequent reaction vessel is not used, the reaction stream from the first reactor is passed directly to the reaction zone column.

The reaction stream, whether from the first reactor or from the subsequent reaction vessel where present, may be passed directly to the reaction zone column or, in one arrangement, it may be first treated for crude removal of the water, and optionally, excess alkanol.

The water removed from the product stream may include water from the feed and also water of esterification. In one arrangement, all water may be removed. However, generally it will be sufficient to reduce the water content such that the feed to the reaction zone column has a water content of less than 10 wt %, particularly about 5 to about 6 wt %.

Any suitable treatment means may be provided. In one arrangement, a flash/distillation column may be used. A flash/distillation column will be particularly useful if the bio-succinic acid is provided to the first reactor as an aqueous solution as this will allow the bulk of the water added with the feed to be removed before the feed is fed to the reaction zone column.

Additionally or alternatively, the temperature of the reaction stream may be adjusted as required before being added to the reaction zone column.

The reaction feed to the reaction zone column is added at or near the top of the reaction zone column. It then passes downwardly through the reaction zone column where it contacts upflowing alkanol. As the reaction feed flows downwardly through the reaction zone column it meets progressively drier alkanol which drives the reaction equilibrium towards the desired dialkyl succinate. The additional alkanol is fed at or near to the bottom of the reaction zone column.

The reaction zone column may be operated at any suitable reaction conditions to assist the furtherance of the reaction. An overheads pressure of about 1.3 bara to about 10 bara. Pressures of 5 bara, 6 bara, 7 bara, 8 bara, 9 bara and 10 bara may be used. A pressure of about 7 bara may offer certain advantages particularly where the alkanol is methanol. The pressure is selected to allow sufficient alkanol concentration to be retained in the liquid phase at the required reaction temperature.

Any suitable reaction temperature may be used. In one arrangement the reaction zone column may operate at a temperature of about 100° C. to about 300° C. Particular advantages may be noted where a temperature of about 120° C. to about 200° C. is used. A temperature of about 150° C. may be particularly advantageous. The temperature in the column sump may be about 190° C. to about 250° C. while the temperature in the overheads of the column may be about 90° C. to about 180° C.

The overall ratio of alkanol to succinic acid, including that used in the first reactor will be in the region of about 3:1 to about 10:1. It will be understood that this is above the stoichiometric ratio for the esterification of 2:1.

Any suitable configuration of reaction zone column may be used. In one arrangement, a divided wall column may be used. In this arrangement, the feed from the first reactor and the recycle stream from the bottoms separation zone will be fed to opposite sides of the wall.

The reaction in the reaction zone column may be carried out in the absence of a catalyst such that it is auto-catalysed. In an alternative arrangement, a catalyst may be used. In one arrangement, the catalyst may be located in the sump of the reaction zone column. In an alternative arrangement, the catalyst may be located in the upper stages of the reaction zone column.

In one arrangement, an alkanol wash may be applied at or near the top of the reaction zone column. This will assist in reducing di-ester losses in the overhead stream removed from the reaction zone column. Where the bio-succinic acid feed is fed in combination with maleic acid or maleic anhydride, a wash of mono-alkyl maleate may be applied at or near the top of the reaction zone column. This will be beneficial in terms of reducing any di-alkyl succinate carryover in the overheads.

The stream removed from at or near the bottom of the reaction zone column is passed to a bottoms stream separation zone. This stream comprises the desired di-alkyl succinate and components selected from residual succinic acid, mono-ester, heavy impurities and alkanol. In one arrangement this stream may comprise about 2 to about 10 wt % residual succinic acid and/or about 20 to about 30 wt. % mono-ester.

As the dialkyl succinate is not removed directly from the reaction zone column, as is the case in conventional esterification flowsheets, very high purity alkanol is not required to achieve high purity di-alkyl succinate.

The bottoms stream separation zone may be of any suitable configuration. In one arrangement, separation of the dialkyl succinate may be achieved by hydrogen stripping. In one arrangement, the hydrogen stripping may occur at about 60 bara.

In an alternative arrangement, the bottoms stream separation zone may be a bottoms stream distillation zone which may be operated at an overhead pressure of from about 0.1 bara to about 1 bara. This mild vacuum moderates the temperatures required to allow the separation to occur. The dialkyl succinate is fractionated from the succinic acid, mono-ester and feed impurities and is removed from the column. In one arrangement, the dialkyl succinate is removed as a liquid draw. The liquid draw will generally be removed as a side draw from a point above the feed point to the bottoms stream distillation zone.

The bottoms stream separation zone may be a bottoms stream distillation column. Any suitable arrangement may be used. In one arrangement, a divided wall column may offer some advantages. In particular, it may prevent water getting into the di-alkyl succinate draw. The presence of water is disadvantageous as it can inhibit downstream hydrogenation catalysts.

Alkanol and other light components will be removed as an overhead stream. The recovered alkanol is preferably recycled to one or both of the first reactor and the reaction zone column. In one arrangement, a purge may be taken. This purge may remove light impurities and/or sulphur.

Any residual succinic acid and any mono-ester present will be concentrated in the bottoms. Impurities will also be present and may be purged. After the purge, the remainder of the column bottoms are preferably recycled to the reaction zone column. They are preferably added to the reaction zone column at a point below the point at which the feed from the first reactor is added.

The temperature of the recycled stream is preferably such that it assists to maintain sufficiently high temperatures on the reaction stages such that the need for side heaters may be obviated.

The overhead from the reaction zone column comprising alkanol, water and organic components, is passed to a top stream distillation zone which may be a top stream distillation column. In one arrangement, the stream may be passed through a condenser, or part condenser, before being passed to the top stream distillation column. This enables useful heat to be recovered and will reduce the cooling water load on the top stream distillation column.

Since the reaction zone column bottoms stream is only part converted some slippage of water into the alkanol recycle may be permitted. This will reduce the heat duty and number of stages required in the top stream distillation column.

In one arrangement, two or more alkanol draws may be taken. These will generally be of different purities. These may be recycled to appropriate places in the reaction system. Conventionally, these alkanol draws will be liquid draws particularly where the alkanol is methanol. The liquid stream will generally be required to be pumped to the point at which it will be used. In one arrangement, at least one of the alkanol draws may be removed as a vapour draw. Generally the vapour draw will be compressed before being pumped to the point at which it will be used. By this means, the condenser duty on the top stream distillation column can be reduced. Where the vapour draw is returned to the reaction zone column, having it as a vapour draw will reduce the vaporisation duty for the reboiler of the reaction zone column.

The top stream distillation zone, which may be a column, may be operated under any suitable conditions. In one arrangement, it may be operated at an overhead pressure of about 1.3 bara to about 2 bara.

An alkanol stream will generally be recovered from at or near the top of the top stream distillation column. A purge may optionally be taken to remove light impurities.

A liquid side draw may be taken from the top stream distillation column. The side draw will remove any dialkyl succinate carried over from the reaction zone column. The side draw will also contain water. The side draw may be passed to a separator in which partially immiscible organic and aqueous phases are separated. In one arrangement, the separator is a decanter.

The aqueous phase will generally be returned to the top stream distillation column. In one arrangement, it is returned to the column at a point below the draw point for the liquid side draw. In one arrangement, the return point will be close to, but below, the draw point. With this arrangement, the water/dialkyl succinate azeotrope can be overcome and di-ester slippage into the aqueous columns bottom is minimised. The organic phase from the separator is recycled to the reaction zone column.

In one arrangement, the feed to the separator may be cooled. This will improve the phase separation. As the cooling duty is small, in one alternative arrangement, a cooling means, such as a cooling coil, may be located in the decanter.

An interchanger may be used with the returned aqueous phase to recover heat.

The esterification in the reaction zone column and one or both of the distillation zones will generally be performed in separate columns.

In one alternative, the reaction zone column and one or both of the distillation zones may be combined in a single column. In this latter arrangement, the unreacted acid and mono-ester are largely retained in the reaction zone column by the column reflux with only the more volatile ester leaving overhead. A benefit of placing the reaction and separation zones in a single column has the benefit of keeping the recycles within the column.

Certain advantages may be noted where the reaction zone column and the separation zones are located in separate columns since the column overhead pressures can be tailored to the specific requirements of the respective column.

Any suitable alkanol may be used. Generally a $C_1$ to $C_4$ alkanol may be used with methanol or ethanol being preferred and with methanol being particularly preferred.

Where the process of the present invention is linked with a process for the production of 1,4-butanediol, the top stream distillation zone, which may be a top stream distillation column, of the present invention may also be used to process recycle streams containing water and alkanol from the butanediol distillation train. Butanol, which is a by-product of the hydrogenolysis reaction and which will be contained in this stream, may be purged from the top stream distillation column as a side draw. In one arrangement, the butanol purge may be fed to a decanter to separate out any water and alkanol so that they may be returned to the distillation zone.

As the process of the present invention can utilise succinic acid of a lower purity than is conventionally used, such as bio-succinic acid, there are significant savings in the number of purification steps required to be performed on the product of the fermentation process. Thus the costs will be substantially reduced and the succinic esterification plant will be able to supply feed to the butanediol plant at a competitive price in comparison to the conventional maleic anhydride.

In one arrangement, a base anion exchange resin system may be used as a polishing step to remove any residual impurities which may be present and which could poison any catalyst used in downstream reactions. In particular, it will be particularly useful in removing any sulphur which may be present. This polishing step will also act as a guard bed to protect downstream catalyst in the event of slippages in the operation of the present invention or in the succinic acid process upstream. In one arrangement the exchange resin could be a sacrificial system in which case it will generally be constructed for ease of replacement. In an alternative arrangement, it will include a regeneration system with a weak base solution.

The condensing requirement for the alkanol may be reduced by using mechanical vapour re-compression of any alkanol recycle stream such that it can be introduced directly into the bottom of the reaction zone column.

Whilst the present invention has been described with reference to a purpose-built plant, it will be understood that conventional plants, such as, for example, those built to operate the processes described in U.S. Pat. No. 4,795,824 and WO 90/08127, may be adapted to use the present invention.

The dialkyl succinate produced in the present invention may be used in the production of 1,4-butanediol, tetrahydrofuran and/or γ-butyrolactone. In addition, it may be used in other processes such as in the manufacture of pharmaceuticals, agrochemicals, perfumery products, plastics, coatings, dyes, pigments, printing inks and other organic compounds. Further it may be hydrolysed back to succinic acid. In this case, the acid will have a higher purity than the acid fed to the present invention.

The present invention will now be described by way of example with reference to the accompanying drawings in which.

It will be understood by those skilled in the art that the drawings are diagrammatic and that further items of equipment such as reflux drums, pumps, vacuum pumps, temperature sensors, pressure sensors, pressure relief valves, control valves, flow controllers, level controllers, holding tanks, storage tanks, and the like may be required in a commercial plant. The provision of such ancillary items of equipment forms no part of the present invention and is in accordance with conventional chemical engineering practice.

The invention will be discussed with reference to the methylation of succinic acid. However, it is equally applicable to the use of other alkanols.

Figure 1:
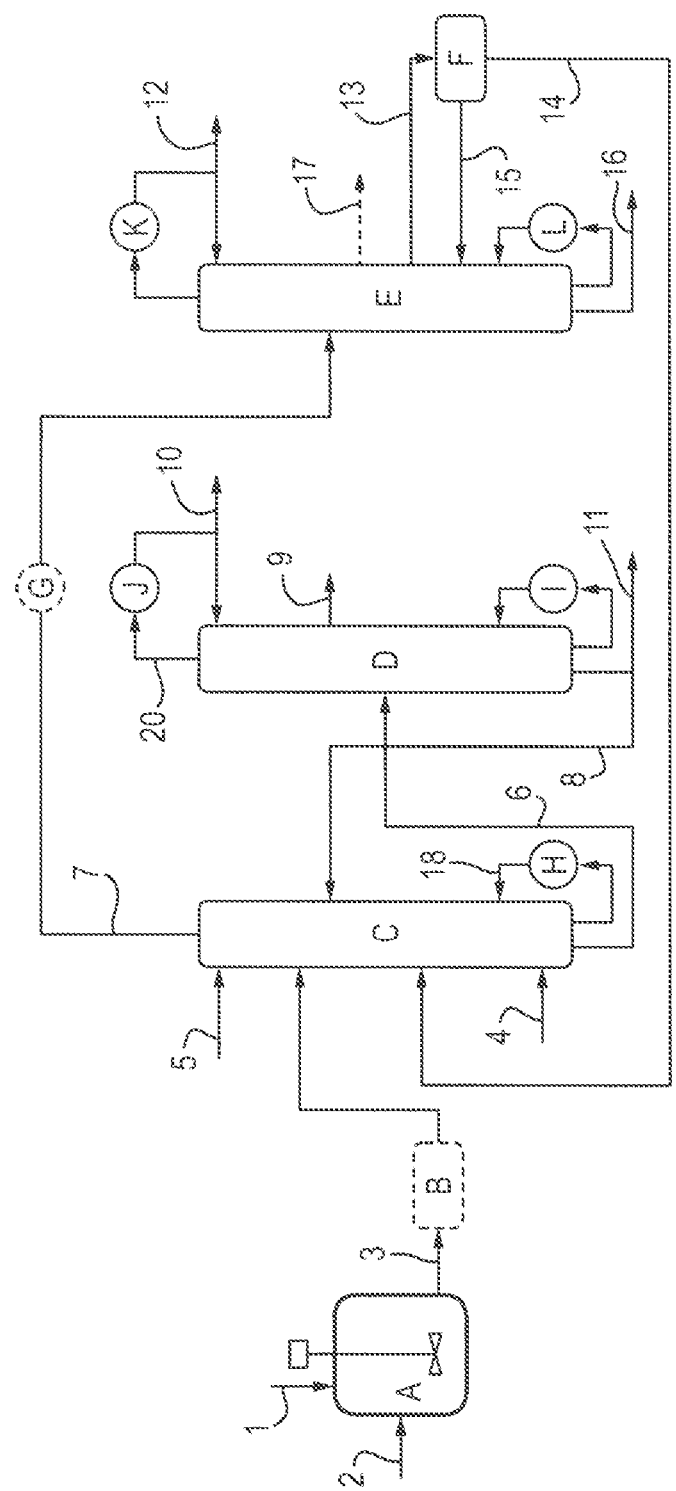
FIG. 1 is a schematic illustration of a flow sheet according to the present invention.

As noted in FIG. 1, succinic acid crystals supplied in line 1 are introduced to a continuous stirred tank reactor A operating at above atmospheric pressure by means of a lock hopper system. Methanol is added in line 2. The succinic acid is simultaneously dissolved in and reacted with the methanol. A product stream 3 from the continuous stirred tank reactor A comprises a part converted mixture of dissolved succinic acid, mono-ester, di-ester, methanol and water. This is optionally passed to a plug flow reaction vessel B where further conversion from mono to di-ester occurs. In an alternative, arrangement, the bio-succinic acid may be added as a slurry or solution. The solution may be a solution in methanol or in water.

Figure 2:
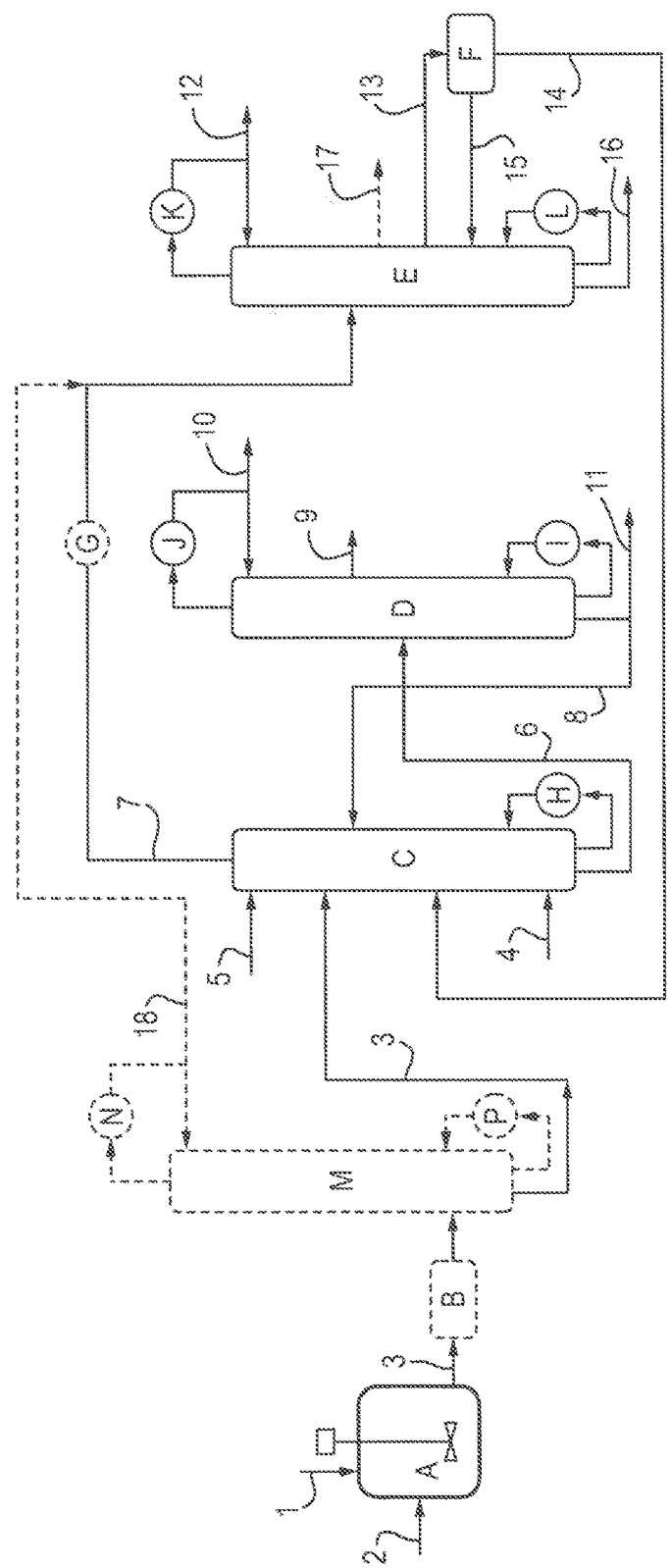
FIG. 2 is a schematic illustration of a modified flow sheet of the present invention.

As illustrated in FIG. 2, the product stream from the continuous stirred tank reactor may optionally be passed to distillation column M where the water may be separated from the stream. The water will be removed in line 18 and passed through condenser N. A portion will be returned to the column M as reflux. The remainder will be passed to top stream distillation zone E as discussed below. A reboiler P may be present at the base of the column M.

The pre-converted feed in line 3 whether fed directly from continuous stirred tank reactor A or via optional plug flow reaction vessel B and/or distillation column M is fed near to the top of the reaction zone column C where it flows downwardly to react counter-currently with upflowing methanol which is fed to the base of the reaction zone column C in line 4. A reboiler H may be located at the base of the reaction zone column C. A methanol wash may be applied to the reaction zone column C in line 5.

A stream comprising the reaction zone column bottoms is removed in line 6 and passed to the bottom stream separation column D. A liquid draw 9 comprising the dialkyl succinate is removed from the bottom stream separation column D above the point at which line 6 is introduced. The bottom stream separation column D may include a reboiler I and an overhead condenser J.

Methanol and other light components are removed from the bottom stream separation column D as an overhead stream 10 and may be recycled to the continuous stirred tank reactor A or the reaction zone column C. A lights purge, not shown, may be removed. Succinic acid and mono-ester are concentrated in the bottom of the column and removed in line 8. Impurities from the feed are purged in line 11. The rest of the column bottoms are recycled in line 8 to the reaction zone column and introduced below the pre-converted feed which is added in line 3.

The overheads from the reaction zone column C are passed in line 7 to the top stream distillation zone E. They may optionally first be passed through condenser G. Methanol is removed in stream 12. A liquid side draw 13 is generally taken from the top stream distillation zone E. The side draw stream will include any di-ester carried over from the reaction zone column C. The stream which also includes water is passed to decanter F in which partially immiscible organic and aqueous phases are separated. The aqueous phase is returned to the top stream distillation zone E in line 15 just below the draw point 13. Water is removed from the column in line 16. The organics phase is recycled to the reaction zone column C in line 14. A reboiler L and a condenser K may be present on the top stream distillation column E.

Where the top stream distillation zone is used to process recycle streams containing water and methanol from a butanediol distillation train, butanol may be purged as a liquid draw in line 17. A decanter, not shown, may be used to separate butanol from methanol and water which may be recycled.

The present invention will now be described with reference to the following examples.

Background Example 1—Deactivation of Esterification Catalyst by Bio-Succinic Acid A 1 liter autoclave was charged with Myriant bio-succinic acid (500 g, 4.2 mol) and methanol (149 g, 4.7 mol, 1.1 equivalent). The vessel was sealed, pressurised to 40 bar(g) under nitrogen and heated to 200° C. at which point the reaction mixture was agitated by stirring at 300 rpm. After 3 hours the vessel was cooled and the product discharged as a light-brown slurry. This process was repeated until sufficient monomethyl succinate had been prepared for further esterification testwork.

The testwork was repeated to obtain discrete samples of monomethyl succinate derived from crude and pure Myriant bio-succinic acid samples.

A 500 ml reaction vessel was charged with 300 g of the crude bio-mono-methyl succinate and 30 g of DPT-2 resin (available from Johnson Matthey Davy Technologies Limited). The vessel was then heated to give an approximate pot temperature of 115° C., with the flange heated to a temperature of 120° C. to reduce internal reflux. Methanol was then introduced directly into the liquor at 3 molar equivalents per hour. The resulting vapour was removed and condensed. Samples of the liquor were taken with time and analysed by titration against 0.1 M potassium hydroxide using phenolphthalein as the indicator and acetone as the solvent. The reaction was continued until the monomethyl succinate concentration was <0.5 wt %.

Figure 3:
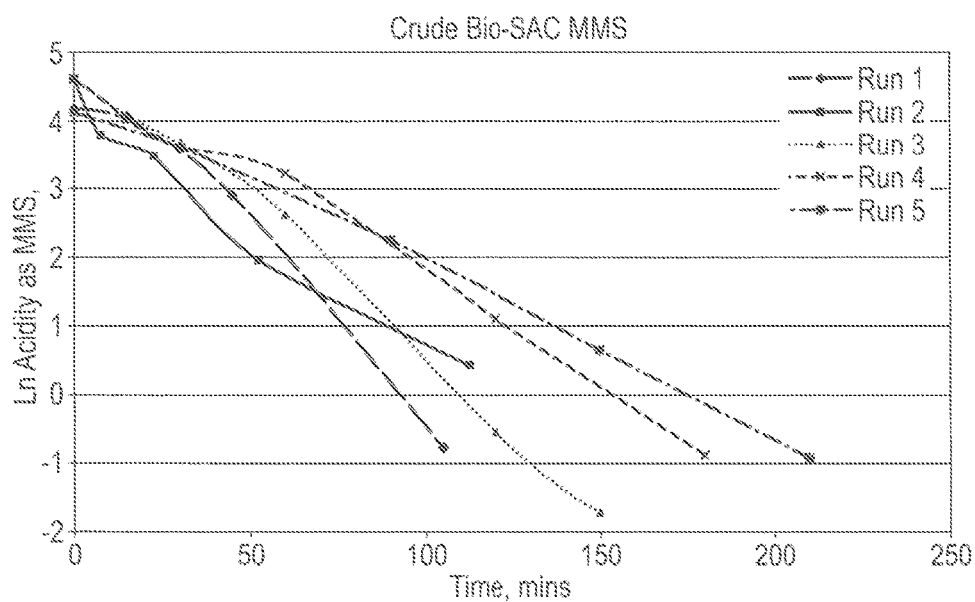
FIG. 3 is a graph giving the results of Background Example 1.

The experiment was repeated to give 4 runs, the results of which can be seen in FIG. 3. The results of the testwork suggest that there was deactivation of the resin with the crude Myriant succinate.

Analysis of the deactivated resin by XRF indicated the presence of relatively large amounts of Fe, however, this was not seen in the crude bio-monomethyl succinate.

Background Example 2

Figure 4:
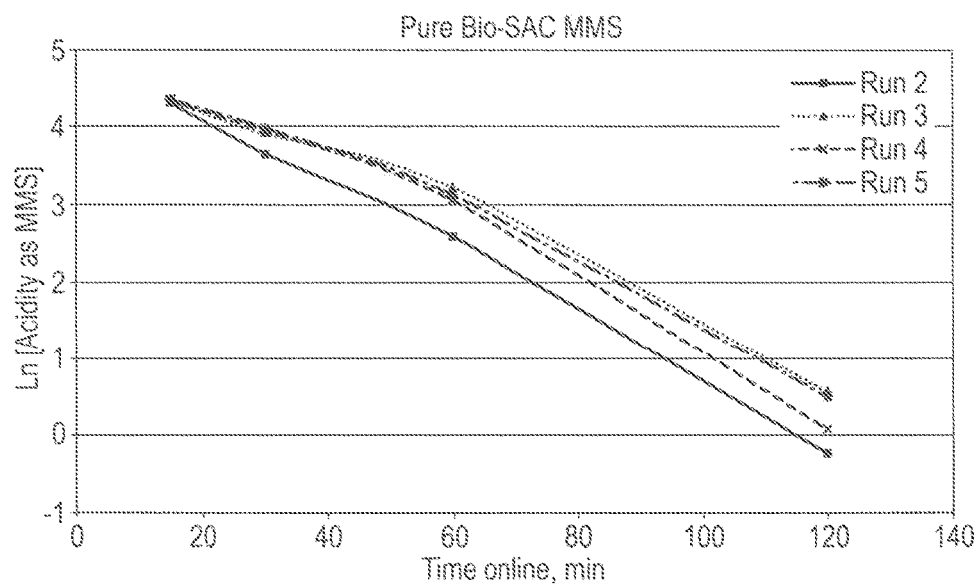
FIG. 4 is a graph giving the results of Background Example 2.

The experiment described above was repeated using bio-monomethyl succinate derived from pure Myriant bio-succinic acid. Five repeat runs were performed using the same charge of ion exchange resin, the results of which can be seen in FIG. 4. The results indicate that there is little deactivation of the resin with the purer material.

To confirm the efficacy of the experiments on the Myriant bio-succinic acid samples the process described above was repeated, for a mono-ester feed derived from maleic anhydride. To a 3-necked round-bottomed flask was added maleic anhydride (2 kg, 20.4 mol). The vessel was heated to 60° C. with stirring, at which point methanol (784 g, 3 mol equivalent) was added drop-wise, maintaining an exotherm of less than 10° C. Once the methanol addition was complete the vessel was crash cooled under running water and discharged.

Background Example 3

Figure 5:
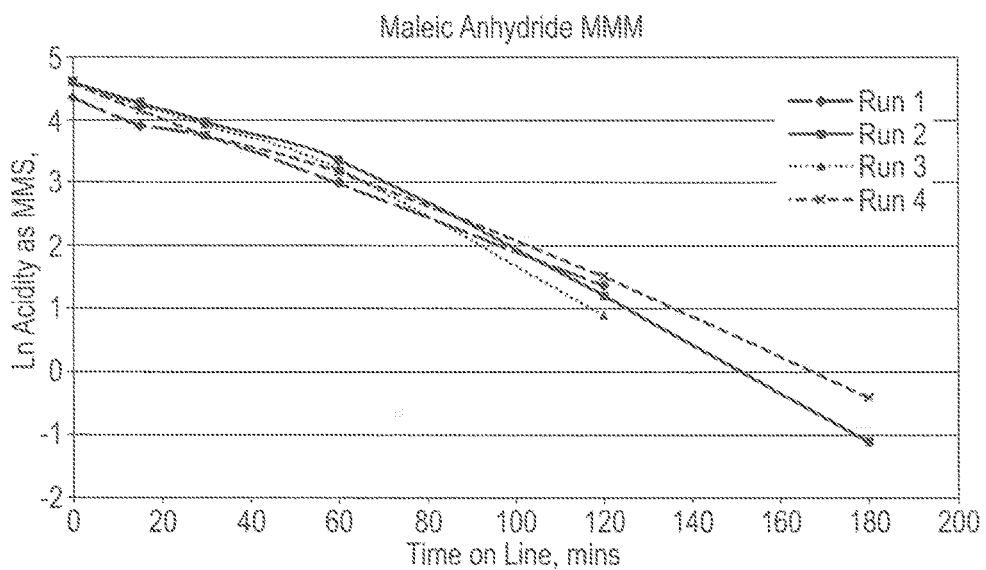
FIG. 5 is a graph giving the results of Background Example 3.

Four repeat esterifications were performed using the monomethyl maleate synthesised above according to the procedure described previously using the same sample of resin. There was no evidence of deactivation as illustrated in FIG. 5.

EXAMPLE 1—DISTILLATION OF BIO-MONOMETHYL SUCCINATE/DIMETHYL SUCCINATE

A 500 ml 3 necked round bottomed flask was charged a dimethyl succinate/monomethyl succinate mixture synthesized using the mono ester preparation method described in Background Example 1 with a 2:1 methanol to bio-succinic acid ratio. The vessel was placed under vacuum (<50 mmHg) and heated to a maximum temperature of 180° C. over time. The initial overheads fractions were liquid at room temperature (methanol and dimethyl succinate), however, over time a white crystalline solid began to form on the condenser (monomethyl succinate). At this point the cooling water was reduced and the condenser was heated to 70° C. the combined overheads were collected as a colourless liquid which contained 37 wt % monomethyl succinate by titration. A black residue of monomethyl succinate remained in the vessel.

Analysis by x-ray fluorescence (XRF) of the liquid feed and overhead product showed that levels of metal and chloride impurities in monomethyl succinate derived by bio-succinic acid can be significantly reduced by simple distillation. The results are set out in Table 1.

TABLE 1

| Metal/Element | Feed Before Distillation (ppm) | Overheads After Distillation (ppm) |
|---|---|---|
| Silicon | 334 | <120 |
| Chromium | 34 | 14 |
| Iron | 41 | 18 |
| Calcium | 230 | 186 |
| Phosphorous | 479 | 495 |
| Chloride | 78 | 37 |

EXAMPLE 2

A 10 liter flask was charged with 5000 g (156.25 mol) of methanol with stirring. 3000 g of bio-succinic acid A (25.42 mol), was slowly charged to the flask. This was heated under reflux at 70° C. for 4 hours until all the bio-succinic acid had dissolved. A further 2000 g (16.95 mol) of bio-succinic acid was added and stirred. The configuration was changed from reflux to a standard continuous stirred tank reactor set up with the ½ inch glass column attached to minimise dimethyl succinate losses. This was heated to 115° C. and methanol was then pumped in at 7 mLmin$^{-1}$.

Reactor samples were taken at regular intervals for wt % acid (as monomethyl succinate) until equilibrium was reached. The equilibrium point was typically 8-12 wt % monomethyl succinate by titration. The crude dimethyl succinate was cooled and the contents discharged. This process was repeated. Three batches (Nos. 1-3) of crude dimethyl succinate were produced for distillation. The same procedure was repeated for 6 batches (Nos. 4-9) of bio-succinic acid B and for 6 batches (Nos. 10-15) of bio-succinic acid C.

Distillation of each of the batches of crude dimethyl succinate was performed using a 1" glass column operated in batch mode.

4000 g of the crude dimethyl succinate was charged to a flask and heated to 180° C. to remove the methanol and water. Once the lights had been removed, the temperature was increased to 200° C. A 2:1 reflux ratio was employed until approximately 300 mL of overheads were obtained. The reflux was then turned off and the remaining material allowed to distill over. Finally the temperature was increased to bring over any remaining dimethyl succinate in the pot.

Mass balances were typically >96 wt % with approximately 90 wt % of the material removed overhead. The dimethyl succinate material that was distilled had an acid content of 0.05 wt % (as monomethyl succinate). This process was repeated until all the crude dimethyl succinate material had been purified by distillation.

The bio-dimethyl succinate material from each of the 15 distillations were analysed for sulphur and chloride. Minimal (ppb) concentrations of chloride were detected in all batches. The sulphur concentrations are detailed in Table 2. It can be seen that distillation of dimethyl succinate from bio-succinic acid samples A and B produced dimethyl succinate with sulphur levels of less than 1 ppm, whilst the distilled dimethyl succinate from Bio-succinic acid C has a substantially higher sulphur level.

TABLE 2

Esterification of bio-succinic samples A, B & C and Batch Distillation of the resulting dimethyl succinate.

| | Sulphur level ppm wt | | |
|---|---|---|---|
| | Bio-succinic acid A (Batch 1) | Bio-succinic acid B (Batch 5) | Bio-succinic acid C (Batch 14) |
| Esterification | | | |
| Succinic acid crystals | 6 | 18 | 159 |
| Crude dimethyl succinate | 2 | NA | 89 |
| Distillation | | | |
| Light fractions | 1.6 | 1.8 | 370 |
| Dimethyl succinate fractions | 0.2 | 0.3 | 18 |
| Residue | NA | 4.8 | 795 |

A hydrogenation reactor was charged with 250 mL of catalyst of 1.45 for catalyst DRD-92/89-A and 1.35 for PG-85/1. Both catalysts are available from Johnson Matthey Davy Technologies Ltd Dimethyl maleate (85 wt %) produced from maleic anhydride and methanol was fed to the reactor to provide an initial activity check prior to the bio-succinic acid being introduced. This was to confirm catalyst performance.

Distilled bio-dimethyl succinate made from bio-succinic acid samples A & B, with a low sulphur concentration (ppb) was introduced. The feed composition was 85 wt % DMS and 15 wt % methanol. The reactor was operated at the following conditions:

| Exit Temperature, ° C. | 190 |
|---|---|
| Pressure, psi (g) | 885 |
| LHSV, hr$^{-1}$ | 0.34 |
| H$_2$:Ester (molar) | 350:1 |

This process gave a dimethyl succinate conversion of 99.67 mol %, with selectivity to tetrahydrofuran, butanol, γ-butyrolactone and butanediol of 3.91 mol %, 0.97 mol %, 11.77 mol % and 83.24 mol % respectively.

The results indicate that the conversion was slightly higher on bio-dimethyl succinate feed compared to dimethyl maleate feed (99.67 vs. 99.13 mol % respectively). The butanol selectivity was marginally higher for the dimethyl succinate feed (0.97 vs. 0.87 mol %). The upper limit for butanol selectivity is 2.0 mol %.

A second run was performed using the same bio-dimethyl succinate feedstock at an increased LHSV to reduce conversion and assess selectivity. The feed rate was increased to a LHSV of 0.5 hr-1. All other parameters remained consistent with the run described above. The feed composition was 85 wt % dimethylsuccinate and 15 wt % methanol. The reactor was operated at the following conditions:

| | |
|---|---|
| Exit Temperature, ° C. | 190 |
| Pressure, psi (g) | 885 |
| LHSV, hr-1 | 0.5 |
| H2:Ester (molar) | 350:1 |

Operation at these conditions resulted in a dimethyl succinate conversion of 97.78 mol %, with selectivity to tetrahydrofuran, butanol, γ-butyrolactone and butanediol of 3.33 mol %, 0.65 mol %, 13.30 mol % and 82.48 mol % respectively. Results from the dimethyl maleate activity check and the two runs on bio-dimethyl succinate made from bio-succinic acid samples A & B are given in Table 3.

The results indicate that the activity dropped approximately 3% after the bio-dimethyl succinate feed was first introduced. The bio-dimethyl succinate feed results in a slower deactivation rate than a commercial dimethyl maleate test.

TABLE 3

Results of Vapour Phase Hydrogenation of Distilled Dimethylsuccinate made from Bio-succinic Acid Samples A & B

| Run ID | Activity Check | Dimethyl succinate | Dimethyl succinate High LHSV |
|---|---|---|---|
| Feed | Dimethyl maleate | bio-dimethyl succinate from bio-succinic acid A & B | bio-dimethyl succinate from bio-succinic acid A & B |
| Time-on-Line, h | 141 | 197 | 378 |
| LHSV, h$^{-1}$ | 0.342 | 0.339 | 0.496 |
| Pressure, psi (g) | 885 | 884 | 885 |
| Inlet Temp, ° C. | 176.5 | 185.5 | 186.1 |
| Exit Temp, ° C. | 190.2 | 190.0 | 190.2 |
| H$_2$: Ester | 344 | 354 | 350 |
| Residence Time, s | 6.16 | 6.29 | 4.35 |
| Analysis, wt % | | | |
| Methanol | 50.28 | 52.33 | 51.60 |
| Tetrahydrofuran | 1.48 | 1.47 | 1.23 |
| Butanol | 0.35 | 0.37 | 0.25 |
| γ-butyrolactone | 5.70 | 5.30 | 5.90 |
| Butanediol | 39.30 | 39.25 | 38.28 |
| Dimethyl succinate | 0.68 | 0.26 | 1.71 |
| Water | 1.09 | 0.70 | 0.67 |
| Unknowns | 0.10 | 0.06 | 0.16 |
| Selectivity, mol % | | | |
| Dimethyl succinate Conversion | 99.13 | 99.67 | 97.78 |
| Tetrahydrofuran Selectivity | 3.83 | 3.91 | 3.33 |
| Butanol Selectivity | 0.873 | 0.97 | 0.65 |
| γ-butyrolactone Selectivity | 12.43 | 11.77 | 13.30 |
| Butanediol Selectivity | 81.84 | 83.24 | 82.48 |

EXAMPLE 3

Succinic acid crystals with up to 160 ppm sulphur were made up to a dimethyl succinate feed for hydrogenation using the procedure described above. The resulting dimethyl succinate was also clear and colourless, but its sulphur level was around 40 ppm, far in excess of the normal 1 ppm limit; this material rapidly deactivated the hydrogenation catalyst when introduced as feed.

Following a second activity check of the hydrogenation catalyst with dimethyl maleate feed, another bio-dimethyl succinate run was performed at an increased LHSV of 0.4 hr$^{-1}$. The bio-dimethyl succinate batches 10-15 (excluding 14), made from bio-succinic acid C as described in Example 2 were blended together. The feed contained a sulphur concentration of 33 ppm. The feed composition was 85 wt % dimethyl succinate and 15 wt % methanol. The reactor was operated at the following conditions:

| | |
|---|---|
| Exit Temperature, ° C. | 190 |
| Pressure, psi (g) | 885 |
| LHSV, hr$^{-1}$ | 0.4 |
| H$_2$:Ester (molar) | 350:1 |

Operation at these conditions on the bio-dimethyl succinate feed resulted in a rapid deactivation of the catalyst. The dimethylsuccinate conversion reduced from 99.05 mol % to 90.52 mol % before the feed was exhausted. Results from the dimethyl maleate activity check and the run on (once distilled) bio-dimethyls succinate made from bio-succinic acid samples C are given in Table 4.

TABLE 4

Results of Vapour Phase Hydrogenation of (once) Distilled Dimethyl Succinate made from Bio-succinic Acid Sample C

| Run ID | Activity Check | Dimethyl Succinate High LHSV |
|---|---|---|
| Feed | Dimethyl maleate | bio-dimethyl succinate from bio-succinic acid C |
| Time-on-Line, h | 697 | 823 |
| LHSV, h$^{-1}$ | 0.337 | 0.400 |
| Pressure, psi (g) | 885 | 884 |
| Inlet Temp, ° C. | 174.7 | 187.4 |
| Exit Temp, ° C. | 190.0 | 189.9 |
| H$_2$: Ester | 349 | 348 |
| Residence Time, s | 4.18 | 5.44 |
| Analysis, wt % | | |
| Methanol | 51.55 | 50.97 |
| Tetrahydrofuran | 1.23 | 1.43 |
| Butanol | 0.35 | 0.33 |
| γ-butyrolactone | 5.52 | 6.15 |
| Butanediol | 39.53 | 33.00 |
| Dimethyl succinate | 0.73 | 7.07 |
| Water | 0.62 | 0.59 |
| Unknowns | 0.06 | 0.18 |
| Selectivity, mol % | | |
| Dimethyl succinate Conversion | 99.05 | 90.52 |
| Tetrahydrofuran Selectivity | 3.24 | 4.28 |
| Butanol Selectivity | 0.89 | 0.95 |
| γ-butyrolactone Selectivity | 12.20 | 15.37 |
| Butanediol Selectivity | 83.48 | 78.76 |

EXAMPLE 4

High sulphur dimethyl succinate from Example 3 was purified to a level where it would be suitable for feed to hydrogenation by performing a more rigorous distillation.

A second distillation was performed on the distilled dimethyl succinate from batch 14 of the bio-succinic acid C which had a high sulphur concentration (18 ppm) after the first distillation (as described in Example 3). A 5 liter flask was charged 2766 g of dimethyl succinate which had already undergone a previous distillation as described above. The temperature was slowly increased to afford a process temperature of 200° C. Both the top and bottom column heaters were set to maintain the process temperature inside the column to minimise heat loss. A 10:1 reflux ratio was employed to attempt to fractionate the sulphur species. A total of 8 overhead fractions were obtained using a 10:1 reflux ratio.

The sulphur content of the fractions were measured and the concentrations are reported in Table 5 below. A high concentration of sulphur was noted in the first fraction (50 ppm) with ppb levels in all subsequent fractions. The pot contents contained a sulphur concentration of 35 ppm. Mass balances for this second distillation were >98 wt % with approximately 78 wt % of the material removed overhead. The sulphur component balance was >99%.

TABLE 5

Repeat Distillation of Dimethyl Succinate Fraction of Bio-Succinic Acid C (Batch 14)

| | Weight (g) | Sulphur level ppm wt |
|---|---|---|
| Feedstock (from 1$^{st}$ distillation) | 2766 | 14 |
| Fraction 1 (Lights) | 348 | 50 |
| Fraction 2 (dimethyl succinate) | 336 | 1 |
| Fraction 3 (dimethyl succinate) | 269 | 1.2 |
| Fraction 4 (dimethyl succinate) | 268 | 0.7 |
| Fraction 5 (dimethyl succinate) | 265 | 0.7 |
| Fraction 6 (dimethyl succinate) | 258 | 0.3 |
| Fraction 7 (dimethyl succinate) | 299 | 0.4 |
| Fraction 8 (dimethyl succinate) | 115 | 0.7 |
| Residue | 572 | 35 |

EXAMPLE 5

High sulphur dimethyl succinate from Example 4 was purified by treating it with a weak base anion exchange resin (Dow IRA-67) which reduced its sulphur content to an acceptable level for feeding to hydrogenation.

Samples of the high sulphur distilled dimethyl succinate made from Bio-succinic acid C (described in Examples 3 & 4) were treated with Amberlite IRA67 (base resin) with the intention of removing the sulphur from the dimethyl succinate.

Oven dried IRA67 was added to each of the dimethyl succinate samples and shaken at regular intervals for 2-3 hours. Each sample was left to stand for 1 hour and a sample of dimethyl succinate was taken for sulphur analysis. The results of sulphur analysis before and after treatment with IRA67 are presented in Table 6.

TABLE 6

IRA67 Treatment of Dimethyl Succinate samples from Bio-Succinic Acid C

| | Sulphur Level (ppb) | |
|---|---|---|
| Sample | Before Treatment | After Treatment |
| Dimethyl succinate Fraction from Distillation 1 of Batch 14 | 12,000 | 883 |

TABLE 6-continued

IRA67 Treatment of Dimethyl Succinate samples from Bio-Succinic Acid C

| | Sulphur Level (ppb) | |
|---|---|---|
| Sample | Before Treatment | After Treatment |
| Fraction 1 from Distillation 2 of Batch 14 | 42,000 | 1,000 |
| Fraction 2 from Distillation 2 of Batch 14 | 1,450 | 661 |
| Pot Residual from Distillation 2 of Batch 14 | 30,000 | 9,840 |
| Blend of dimethyl succinate fractions from Distillation 1 of batches 10-13 & 15. | 33,000 | 743 |

EXAMPLE 6

This example demonstrates esterification of succinic acid with methanol at temperatures of 190-210° C. in batch autoclaves.

Studies on succinic acid conversion were undertaken using 6×100 cm$^3$ Hastelloy™ autoclaves each containing a cross-shaped magnetic follower. Heating was provided by a metallic block-heater which was close-fitted to each autoclave. Heating was controlled by a suitable temperature controller and each autoclave was individually magnetically stirred. The block was pre-heated to the desired reaction temperature prior to the addition of the autoclaves.

Each autoclave was individually charged with the desired starting composition of succinic acid and methanol (up to 30 g) and the resulting suspension sealed and pressured with 150 psig $N_2$ at room temperature, to minimise component vapour losses during reaction. The autoclaves were leak-tested for 45 minutes and all six placed into the pre-heated block together. An initial run had determined that a maximum autoclave pressure (ca. 390 psig at 190° C.) was obtained after 25 minutes in the heated block (30 minutes at 210° C.) and these timings were therefore used as the "T=0" start times for sampling.

Autoclaves were then removed from the block upon reaching their desired sample timings and immediately submerged in ice-water for 15 minutes in order to rapidly quench the reaction. Mass balances were calculated from comparison of the autoclave masses after reaction (vented) with that of the empty autoclave. All samples were analysed for water (coulometric Karl-Fisher) and by GC (Regisil-treated, 50 m DB-1 column, HY 381 method).

Starting molar compositions of succinic acid to methanol of 1:2 and 1:4 were employed at reaction temperatures of 190° C. and 210° C., above the melting point of succinic acid. Data was collected at 10 or 15 minute intervals starting from T=0 giving data for 50 or 75 minutes per run. Mass balances were generally good (>98%) which is likely to be due to good retention of volatiles with the cold-sampling method employed. Methanol levels by GC, however, are still considered unreliable due to the rapid exotherm present upon Regisil treatment of samples. This is likely to be due to the high levels of water present in these samples, typically being in excess of 10 wt %.

The data obtained, which is presented in Tables 7-10 shows trends in the components as expected, with greater conversion to dimethyl succinate at increased temperature and increased methanol to succinic acid ratio.

TABLE 7

Results of esterification of succinic acid in a 1:4 ratio with methanol at 190° C. in 6 × batch autoclaves Experiment Description: 1:4, Methanol:Succinic acid - 190° C; 6 × 100 ml Autoclaves Autoclave Charge (per Autoclave)

| Component | Mass/g | RMM/g mol-1 | Mols | Mol Fraction |
|---|---|---|---|---|
| Methanol | 15.2 | 32 | 0.475 | 80.0% |
| Succinic Acid | 14.0 | 118 | 0.119 | 20.0% |
| Totals | 29.2 | | 0.593 | |

| Autoclave Number | N/A | 1 | 2 | 3 | 4 | 5 | 6 |
|---|---|---|---|---|---|---|---|
| Time/min | Initial | 0 | 15 | 30 | 48 | 60 | 75 |
| Mass Discharged/g | | 29.1 | 29.0 | 28.9 | 29.2 | 29.2 | 29.2 |
| Components | | | | | | | |
| Methanol/GC, wt % | 52.033 | 33.304 | 30.328 | 30.221 | 29.618 | 29.014 | 27.828 |
| Dimethyl Succinate/GC, wt % | 0.000 | 19.053 | 30.190 | 34.492 | 42.416 | 37.548 | 37.279 |
| Monomethyl succinate/GC, wt % | 0.000 | 28.830 | 22.852 | 21.035 | 19.242 | 18.684 | 18.480 |
| Succinic acid/GC, wt % | 47.967 | 11.093 | 4.591 | 3.153 | 2.533 | 2.332 | 2.281 |
| Water/KFT, wt % | 0.000 | 7.172 | 9.792 | 10.344 | 13.245 | 11.682 | 13.407 |
| Sum of Knowns | 100.0% | 99.5% | 97.8% | 99.2% | 107.1% | 99.3% | 99.3% |
| Methanol/mol | 1.626 | 1.041 | 0.948 | 0.944 | 0.926 | 0.907 | 0.870 |
| Dimethyl succinate/mol | 0.000 | 0.130 | 0.207 | 0.236 | 0.291 | 0.257 | 0.255 |
| Monomethyl succinate/mol | 0.000 | 0.218 | 0.173 | 0.159 | 0.146 | 0.142 | 0.140 |
| Succinic acid/mol | 0.407 | 0.094 | 0.039 | 0.027 | 0.021 | 0.020 | 0.019 |
| Water/mol | 0.000 | 0.398 | 0.544 | 0.575 | 0.736 | 0.649 | 0.745 |
| MOL Total | 203.3 | 188.2 | 191.1 | 194.1 | 211.9 | 197.4 | 202.9 |
| Methanol/mol fraction | 0.800 | 0.553 | 0.496 | 0.486 | 0.437 | 0.459 | 0.429 |
| Dimethyl succinate/mol fraction | 0.000 | 0.069 | 0.108 | 0.122 | 0.137 | 0.130 | 0.126 |
| Monomethyl succinate/mol fraction | 0.000 | 0.116 | 0.091 | 0.082 | 0.069 | 0.072 | 0.069 |
| Succinic acid/mol fraction | 0.200 | 0.050 | 0.020 | 0.014 | 0.010 | 0.010 | 0.010 |
| Water/mol fraction | 0.000 | 0.212 | 0.285 | 0.296 | 0.347 | 0.329 | 0.367 |
| Mass Balance | 99.7% | 99.7% | 99.4% | 99.0% | 100.0% | 100.0% | 100.0% |
| Methanol Balance | 100.0% | 101.0% | 100.4% | 101.5% | 97.5% | 98.9% | 93.7% |
| Conversion to dimethyl succinate ($C_4$ basis) | 0.0% | 29.5% | 49.4% | 55.9% | 63.5% | 61.5% | 61.6% |

TABLE 8

Results of esterification of succinic acid in a 1:2 ratio with methanol at 190° C. in 6 × batch autoclaves Experiment Description: 1:2, Methanol:succinic acid - 190° C; 6 × 100 ml Autoclaves Autoclave Charge (per Autoclave)

| Component | Mass/g | RMM/g mol-1 | Mols | Mol Fraction |
|---|---|---|---|---|
| Methanol | 7.6 | 32 | 0.238 | 66.7% |
| Succinic Acid | 14.0 | 118 | 0.119 | 33.3% |
| Totals | 21.6 | g | 0.356 | |

| Autoclave Number | N/A | 1 | 2 | 3 | 4 | 5 | 6 |
|---|---|---|---|---|---|---|---|
| Time/min | Initial | 0 | 15 | 30 | 45 | 60 | 78 |
| Mass Discharged/g | N/A | 21.2 | 21.4 | 21.3 | 21.4 | 21.4 | 21.5 |
| Components | | | | | | | |
| Methanol/GC, wt % | 35.185 | 12.062 | 11.235 | 9.940 | 9.704 | 9.468 | 9.165 |
| Dimethylsuccinate/GC wt % | 0.000 | 27.351 | 32.232 | 35.455 | 35.820 | 36.613 | 36.517 |

TABLE 8-continued

Results of esterification of succinic acid in a 1:2 ratio with methanol at 190° C. in 6 × batch autoclaves

| | Experiment Description | 1:2, Methanol:succinic acid - 190° C; 6 × 100 ml Autoclaves | | | | | |
|---|---|---|---|---|---|---|---|
| Monomethylsuccinate/ GC wt % | 0.000 | 36.783 | 33.649 | 32.319 | 32.464 | 31.168 | 31.767 |
| Succinic acid/GC, wt % | 64.815 | 12.571 | 9.831 | 8.585 | 8.181 | 7.766 | 8.115 |
| Water/KFT, wt % | 0.000 | 10.000 | 12.317 | 13.066 | 13.298 | 13.419 | 13.388 |
| Sum of Knowns % | 100.0 | 98.8 | 99.3 | 99.4 | 99.5 | 98.4 | 99.0 |
| Methanol/mol | 1.100 | 0.377 | 0.351 | 0.311 | 0.303 | 0.296 | 0.286 |
| Dimethyl succinate/mol | 0.000 | 0.187 | 0.221 | 0.243 | 0.245 | 0.251 | 0.250 |
| Monomethyl succinate/ mol | 0.000 | 0.279 | 0.255 | 0.245 | 0.246 | 0.236 | 0.241 |
| Succinic acid/mol | 0.549 | 0.107 | 0.083 | 0.073 | 0.069 | 0.066 | 0.069 |
| Water/mol | 0.000 | 0.556 | 0.684 | 0.726 | 0.739 | 0.746 | 0.744 |
| MOL Total | 164.9 | 150.5 | 159.4 | 159.7 | 160.3 | 159.4 | 159.0 |
| Methanol/mol fraction | 0.667 | 0.250 | 0.220 | 0.195 | 0.189 | 0.186 | 0.180 |
| Dimehtyl succinate/ mol fraction | 0.000 | 0.124 | 0.138 | 0.152 | 0.153 | 0.157 | 0.157 |
| Monomethyl succinate/ mol fraction | 0.000 | 0.185 | 0.160 | 0.153 | 0.153 | 0.148 | 0.151 |
| Succinic acid/mol fraction | 0.333 | 0.071 | 0.052 | 0.046 | 0.043 | 0.041 | 0.043 |
| Water/mol fraction | 0.000 | 0.369 | 0.429 | 0.455 | 0.461 | 0.468 | 0.468 |
| Mass Balance % | N/A | 98.1 | 99.1 | 98.6 | 99.1 | 99.1 | 99.5 |
| Methanol Balance % | 100.0 | 102.7 | 98.5 | 97.8 | 97.3 | 97.2 | 96.9 |
| Conversion to Dimethyl succinate ($C_4$ basis) | 0.0 | 32.7 | 39.5 | 43.3 | 43.8 | 45.4 | 44.7 |

TABLE 9

Results of esterification of succinic acid in a 1:4 ratio with methanol at 210° C. in 6 × batch autoclaves

| | Experiment Description | 1:4, Methanol:Succinic acid - 210° C; 6 × 100 ml Autoclaves | | | | | |
|---|---|---|---|---|---|---|---|
| | Autoclave Charge (per Autoclave) | | | | | | |
| Component | Mass/g | RMM/g mol-1 | | Mols | | Mol Fraction | |
| Methanol | 15.2 | 32 | | 0.475 | | 80.0% | |
| Succinic acid | 14.0 | 118 | | 0.119 | | 20.0% | |
| TOTALS | 29.2 | g | | 0.594 | | | |
| Autoclave Number | N/A | 1 | 2 | 3 | 4 | 5 | 6 |
| Time/min | Initial | 0 | 15 | 30 | 45 | 60 | 78 |
| Mass Discharged/g | N/A | 21.2 | 21.4 | 21.3 | 21.4 | 21.4 | 21.5 |
| Components | | | | | | | |
| Methnaol/GC, wt % | 52.055 | 26.547 | 28.503 | 27.002 | 27.633 | 28.177 | 27.437 |
| Dimethyl succinate/ GC. wt % | 0.000 | 30.617 | 34.013 | 37.628 | 38.581 | 38.136 | 40.186 |
| Monomethylsuccinate/ GC wt % | 0.000 | 26.719 | 22.433 | 20.103 | 16.900 | 16.032 | 16.749 |
| Succinic acid/GC, wt % | 47.945 | 5.454 | 3.458 | 2.695 | 1.981 | 1.883 | 1.888 |
| Water/KFT, wt % | 0.000 | 10.222 | 10.809 | 11.561 | 11.785 | 12.221 | 12.657 |
| Sum of Knowns (%) | 100.0 | 99.6 | 99.2 | 99.0 | 96.9 | 96.4 | 98.9 |
| Methanol/mol (%) | 162.7 | 83.0 | 89.1 | 84.4 | 86.4 | 88.1 | 85.7 |
| Dimethyl succinate/mol (%) | 0.0 | 21.0 | 23.3 | 25.8 | 26.4 | 26.1 | 27.5 |
| Monomethyl succinate/ mol (% | 0.0 | 20.2 | 17.0 | 15.2 | 12.8 | 12.1 | 12.7 |
| Succinic acid/mol (%) | 40.6 | 4.6 | 2.9 | 2.3 | 1.7 | 1.6 | 1.6 |
| Water/mol (%) | 0.0 | 56.8 | 60.1 | 64.2 | 65.5 | 67.9 | 70.3 |
| MOL Total | 203.3 | 185.6 | 192.3 | 191.9 | 192.7 | 195.8 | 197.9 |
| Methanol/mol fraction | 0.800 | 0.447 | 0.463 | 0.440 | 0.448 | 0.450 | 0.433 |
| Dimethyl succinate/ mol fraction | 0.000 | 0.113 | 0.121 | 0.134 | 0.137 | 0.133 | 0.139 |
| Monomethyl succinate/ mol fraction | 0.000 | 0.109 | 0.088 | 0.079 | 0.066 | 0.062 | 0.064 |

TABLE 9-continued

Results of esterification of succinic acid in a 1:4 ratio with methanol at 210° C. in 6 × batch autoclaves

| Experiment Description | 1:4, Methanol:Succinic acid - 210° C; 6 × 100 ml Autoclaves | | | | | | |
|---|---|---|---|---|---|---|---|
| Succinic acid/mol fraction | 0.200 | 0.025 | 0.015 | 0.012 | 0.009 | 0.008 | 0.008 |
| Water/mol fraction | 0.000 | 0.306 | 0.312 | 0.335 | 0.340 | 0.347 | 0.355 |
| Mass Balance | N/A | 72.6% | 73.3% | 72.9% | 73.3% | 73.3% | 73.6% |
| Methanol Balance | 100.0% | 97.7% | 99.2% | 98.4% | 98.6% | 97.3% | 96.9% |
| Conversion to dimethyl succinate ($C_4$ basis) | 0.0% | 45.8% | 53.9% | 59.5% | 64.6% | 65.5% | 65.8% |

TABLE 10

Results of esterification of succinic acid in a 1:2 ratio with methanol at 210° C. in 6 × batch autoclaves

| Experiment Description | 1:2 Methanol:Succinic acid - 210° C; 6 × 100 ml Autoclaves | | | | | |
|---|---|---|---|---|---|---|
| Autoclave Charge (per Autoclave) | | | | | | |
| Component | Mass/g | RMM/g mol-1 | | Mols | Mol Fraction | |
| Methanol | 7.6 | 32 | | 0.238 | 66.7% | |
| Succinic acid | 14.0 | 118 | | 0.119 | 33.3% | |
| TOTALS | 21.6 | g | | 0.356 | | |
| Autoclave Number | N/A | 1 | 2 | 3 | 4 | 5 | 6 |
| Time/min | Initial | 0 | 15 | 30 | 48 | 60 | 75 |
| Mass Discharged/g | N/A | 21.3 | 21.4 | 21.4 | 21.3 | 21.6 | 21.4 |
| Components | | | | | | | |
| Methanol/GC, wt % | 35.185 | 11.974 | 10.015 | 9.914 | 10.467 | 9.261 | 9.531 |
| Dimethylsuccinate/GC wt % | 0.000 | 34.477 | 35.544 | 36.478 | 36.246 | 36.944 | 36.116 |
| Monomethylsuccinate/GC wt % | 0.000 | 32.082 | 32.488 | 31.692 | 30.645 | 31.474 | 31.242 |
| Succinic acid/GC, wt % | 64.815 | 8.305 | 8.491 | 8.291 | 7.958 | 8.002 | 7.745 |
| Water/KFT, wt % | 0.000 | 11.989 | 12.521 | 12.915 | 13.787 | 13.919 | 14.111 |
| Sum of Knowns % | 100.0 | 98.8 | 99.1 | 99.3 | 99.1 | 99.6 | 98.7 |
| Methanol/mol % | 110.0 | 37.4 | 31.3 | 31.0 | 32.7 | 28.9 | 29.8 |
| Dimethyl succinate/mol (%) | 0.0 | 23.6 | 24.3 | 25.0 | 24.8 | 25.3 | 24.7 |
| Monomethyl succinate/mol (%) | 0.0 | 24.3 | 24.6 | 24.0 | 23.2 | 23.8 | 23.7 |
| Succinic acid/mol (%) | 54.9 | 7.0 | 7.2 | 7.0 | 6.7 | 6.8 | 6.6 |
| Water/mol (%) | 0.0 | 66.6 | 69.6 | 71.8 | 76.6 | 77.3 | 78.4 |
| MOL Total | 164.9 | 159.0 | 157.0 | 158.8 | 164.1 | 162.2 | 163.1 |
| Methanol/mol fraction | 0.667 | 0.235 | 0.199 | 0.195 | 0.199 | 0.178 | 0.183 |
| Dimthyl succinate/mol fraction | 0.000 | 0.149 | 0.155 | 0.157 | 0.151 | 0.156 | 0.152 |
| Monomethyl succinate/mol fraction | 0.000 | 0.153 | 0.157 | 0.151 | 0.141 | 0.147 | 0.145 |
| Succinic acid/mol fraction | 0.333 | 0.044 | 0.046 | 0.044 | 0.041 | 0.042 | 0.040 |
| Water/mol fraction | 0.000 | 0.419 | 0.443 | 0.452 | 0.467 | 0.477 | 0.481 |
| Mass Balance (%) | N/A | 98.6 | 99.1 | 99.1 | 98.6 | 100.0 | 99.1 |
| Methanol Balance (%) | 100.0 | 102.8 | 99.9 | 99.1 | 96.5 | 95.6 | 94.6 |
| Conversion to DMS ($C_4$ basis) | 0.0% | 43.0% | 43.4% | 44.6% | 45.3% | 45.2% | 45.0% |

Figure 6:
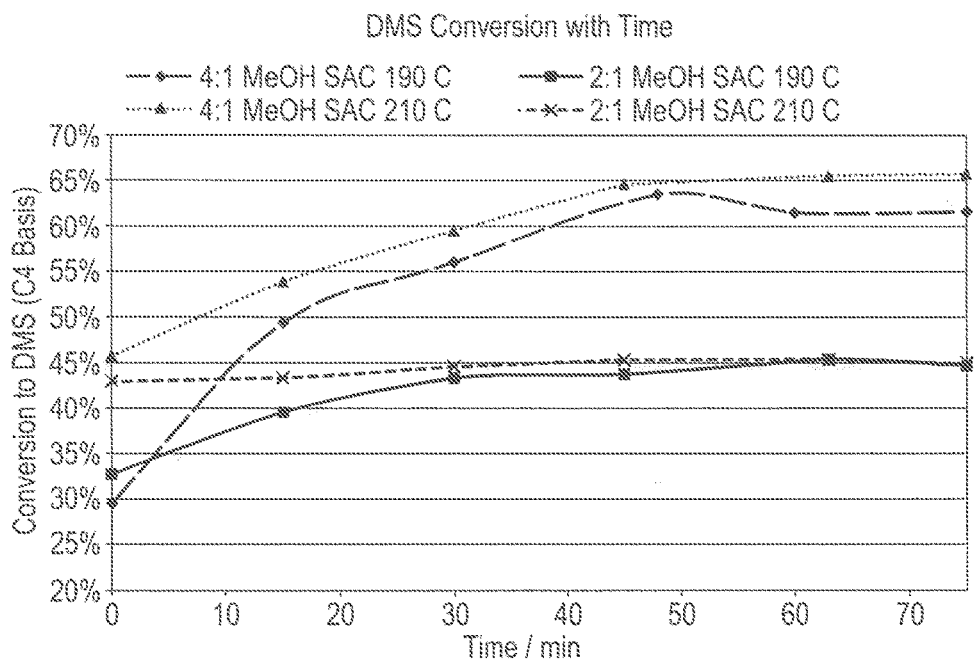
FIG. 6 is a graph giving the results of Example 6.

The results of Example 6 are illustrated in the graph of FIG. 6.

EXAMPLE 7

In this example mono-methyl succinate is esterified with methanol to the di-ester with conversion of almost 90% at a temperature of 190° C.

Figure 7:
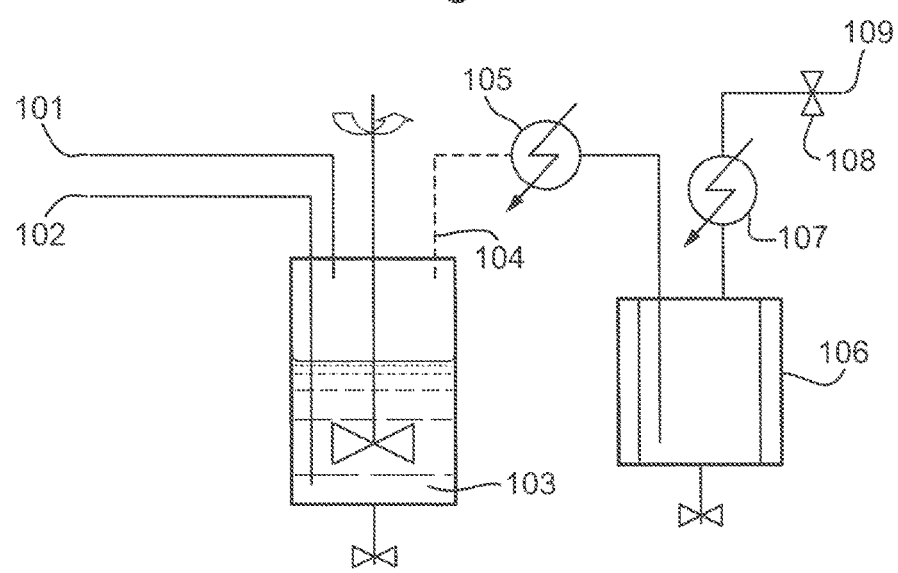
FIG. 7 is a schematic representation of the apparatus used in Example 7.

The monomethyl succinate for this testwork was synthesized in-house from commercially available succinic anhydride and used in its crude form. A 1 dm³ stainless steel autoclave fitted with a bottoms sample point was charged with MMS and made up to 200 psig with nitrogen to minimise component vapour pressures. The reactor was then heated to the desired reaction temperature of 190° C. and methanol pumped to the autoclave via an HPLC pump at a desired rate this was called time zero ("T=0"). Overheads were extracted via an electrically traced heated line to avoid condensation and reflux of the product mixture. This was then condensed and collected via a water cooled catch-pot. This is detailed schematically in FIG. 7. In which 200 psig nitrogen is added in line 101 and methanol is added by pump in line 102. The monomethyl succinate 103 is located in the autoclave. The overheads are removed in trace heated line 104 and then condensed against cooling water in line 105 and then passed to water cooled catch-pot 106. Overhead from the catchpot is also cooled against water stream 107 before being passed through metering valve and bubbler 108 and passing to vent 109. This served to allow a small gas flow through the system whilst maintaining the reactor pressure at 200 psig.

Samples from the autoclave itself and of the overheads collected were taken at periodic time intervals and subsequently analysed for water (coulometric Karl-Fisher) and by GC. Autoclave samples were analysed after Regisil treatment on a 50 m DB-1 column, and overheads directly analysed for methanol and dimethyl ether on a 60 m DB-1 column. Masses of all samples and reactor contents were noted to allow mass balances to be calculated.

A reaction temperature of 190° C. and a feed rate of 2 mols methanol per mole of monomethyl succinate per hour was chosen; 3 mols of monomethyl succinate were charged to the autoclave requiring a methanol flow rate of 4.05 mL min$^{-1}$ for the run. A second run was performed at double this flow rate. When the system was at temperature, methanol flow commenced for 120 minute, with periodic sampling throughout the run. The feed composition and conditions used for each test, Runs 1 & 2 are given in Tables 11 & 14 respectively, while the results are given in Tables 12, 13, 15 and 16.

TABLE 11

Feed composition and test conditions for Run 1 at 2 mol Methanol per hour per mol succinic acid

| Experiment Description | Example 7 Run 1<br>2 mol methanol hr$^{-1}$ per mol succinic acid charged at 190° C. | | | |
|---|---|---|---|---|
| Autoclave Charge (1 L Parr) | | | | |
| Component | Mass, g | RMM/g mol$^{-1}$ | Mol | Mol Fraction |
| Monomethyl Succinate (Crude) | 396.0 | 132 | 3.0 | 1.00 |
| Theoretical Yield (of Dimethyl succinate) | 438.0 | | | |
| Crude Monomethyl succinate Analysis | | | | |
| Component | Mass | RMM/g mol$^{-1}$ | Mols | Mol Fraction |
| Methanol | 0.9 | 32 | 0.027 | 0.01 |
| Dimethyl succinate | 62.5 | 146 | 0.428 | 0.14 |
| Monomethyl succinate | 284.3 | 132 | 2.154 | 0.70 |
| Succinic Acid | 47.4 | 118 | 0.402 | 0.13 |
| Water | 0.9 | 18 | 0.048 | 0.02 |
| Total | 396.0 | | 3.060 | |
| Methanol Flow | | | | |
| Target, molar | 2.0 | mol hr–1 mol$^{-1}$ (MMS) | 6.0 | mol MeOH h$^{-1}$ |
| Flow | 192.0 | g hr$^{-1}$ | | |
| Density (Methanol) | 0.79 | g ml$^{-1}$ | | |
| Target Flow Rate | 4.05 | ml min$^{-1}$ | | |

TABLE 12

Results of Example 7 Run 1

| | Example 7 Run 1 | | | | | | |
|---|---|---|---|---|---|---|---|
| Time, min | 0 | 11 | 22 | 32 | 42 | 52 | 61 |
| Mass Discharged (autoclave), g | 14.5 | 8.3 | 10.4 | 8.2 | 9.8 | 13.6 | 13.0 |
| Methanol Flow Rate/ml min$^{-1}$ | 4.05 | 4.05 | 4.10 | 4.05 | 4.05 | 4.05 | 4.05 |
| Reaction Temperature, ° C. | 190 | 188 | 188 | 188 | 187 | 188 | 187 |
| System Pressure, psig | 169 | 158 | 165 | 165 | 164 | 163 | 167 |
| Autoclave Components | | | | | | | |
| Methanol/GC, wt % | 1.097 | 3.341 | 6.881 | 11.123 | 12.683 | 12.315 | 11.946 |
| Dimethyl succinate/GC, wt % | 29.214 | 33.185 | 41.273 | 46.738 | 50.692 | 54.770 | 58.932 |
| Monomethyl succinate/GC, wt % | 48.730 | 44.418 | 37.632 | 31.405 | 27.408 | 22.714 | 22.849 |
| Succinic acid AC/GC, wt % | 18.440 | 15.476 | 9.613 | 5.918 | 4.152 | 2.745 | 2.416 |
| Water/KFT, wt % | 1.950 | 2.789 | 4.081 | 4.386 | 4.518 | 3.773 | 3.205 |
| Sum of Knowns, % | 99.4 | 99.2 | 99.5 | 99.6 | 99.5 | 96.3 | 99.3 |
| Conversion to Dimethyl succinate (C$_4$ Basis), % | 27.6 | 32.7 | 43.5 | 52.6 | 58.8 | 65.8 | 67.6 |
| Overheads Collected, g | 0.0 | 0.0 | 0.1 | 13.4 | 30.8 | 40.8 | 27.4 |
| Overheads, analysis | | | | | | | |
| Methanol/GC, wt % | | | | 80.939 | 79.238 | 86.252 | 88.699 |
| Dimethyl succinate/GC, wt % | | | | 2.613 | 4.100 | | |
| Monomethyl succinate/GC, wt % | | | | 0.361 | 0.332 | | |
| Succinic acid/GC, wt % | | | | 0.131 | 0.113 | | |

TABLE 12-continued

Results of Example 7 Run 1

| | Example 7 Run 1 | | | | | | |
|---|---|---|---|---|---|---|---|
| Time, min | 0 | 11 | 22 | 32 | 42 | 52 | 61 |
| Water/KFT, wt % | | | | 12.021 | 13.303 | 13.708 | 11.301 |
| Methanol/GC, wt % | | | | | | | |

TABLE 13

Results of Example 7 Run 1 continued

| | Example 7 Run 1 (cont'd) | | | | | | |
|---|---|---|---|---|---|---|---|
| Time, min | 72 | 81 | 91 | 101 | 111 | 121 | Final |
| Mass Discharged (autoclave), g | 16.8 | 11.4 | 13.7 | 15.7 | 16.5 | 12.9 | 731.5 |
| Methanol Flow Rate, ml min$^{-1}$ | 4.10 | 4.05 | 4.05 | 4.05 | 4.05 | 4.05 | |
| Reaction Temperature, °C | 188 | 189 | 188 | 188 | 188 | 190 | |
| System Pressure, psig | 165 | 167 | 166 | 167 | 166 | 161 | |
| Autoclave Components | | | | | | | |
| Methanol/GC, wt % | 11.349 | 13.560 | 12.833 | 12.814 | 12.651 | 13.512 | 13.560 |
| Dimethyl succinate/GC, wt % | 63.176 | 64.074 | 66.316 | 69.566 | 71.106 | 72.303 | 64.074 |
| Monomethyl succinate/GC, wt % | 20.537 | 18.388 | 17.281 | 15.056 | 13.945 | 12.136 | 18.388 |
| Succinic acid/GC, wt % | 1.879 | 1.506 | 1.275 | 0.957 | 0.759 | 0.535 | 1.506 |
| Water/KFT, wt % | 2.511 | 1.941 | 1.550 | 1.073 | 0.920 | 0.822 | 1.941 |
| Sum of Knowns, % | 99.5 | 99.5 | 99.3 | 99.5 | 99.4 | 99.3 | 99.5 |
| Conversion to Dimethyl succinate (C$_4$ Basis), % | 71.6 | 74.3 | 76.2 | 79.6 | 81.3 | 83.7 | 88.2 |
| Overheads Collected, g | 40.4 | 30.2 | 35.2 | 35.5 | 37.9 | 36.8 | 292.8 |
| Overheads, analysis | | 3.4 | 3.5 | 3.6 | 3.8 | 3.7 | |
| Methanol/GC, wt % | 88.838 | 90.803 | 92.240 | 94.859 | 95.399 | 96.787 | 97.165 |
| Dimethyl succinate/GC, wt % | | | | | | | |
| Monomethyl succinate/GC, wt % | | | | | | | |
| Succinic acid/GC, wt % | | | | | | | |
| Water/KFT, wt % | 11.162 | 9.197 | 7.760 | 5.141 | 4.601 | 3.213 | 2.835 |
| Methanol/GC, wt % | | | | | | | |

Figure 8:
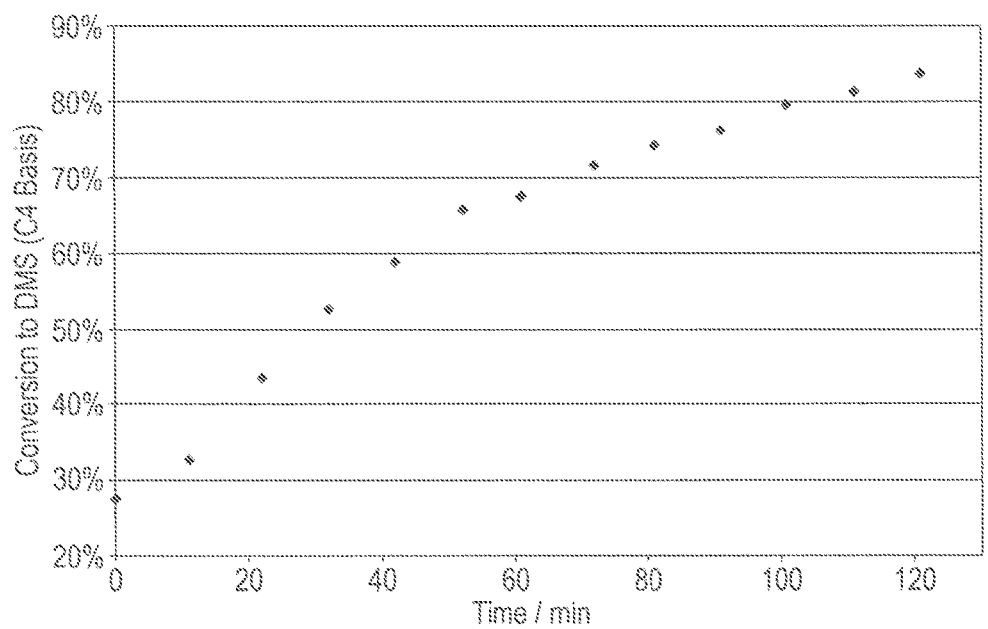
FIG. 8 is a graph giving the results of the Example 7 (run 1).

The results of run 1 of Example 7 are illustrated in FIG. 8.

TABLE 14

Feed composition and test conditions for Example 7 Run 2 at 4 mol Methanol per hour per mol succinic acid

| Experiment Description | Example 7 Run 2<br>4 mol MeOH hr$^{-1}$ per mol SAC charged at 190° C. | | | |
|---|---|---|---|---|

| Autoclave Charge (1 L Parr) | | | | |
|---|---|---|---|---|
| Component | Mass/g | RMM/g mol$^{-1}$ | Mols | Mol Fraction |
| Monomethyl succinate (Crude) | 396.0 | 132 | 3.0 | 1.00 |
| Theoretical Yield (of dimethyl succinate) | 438.0 | | | |

| Crude Monomethyl Succinate Analysis | | | | |
|---|---|---|---|---|
| Component | Mass | RMM/g mol$^{-1}$ | Mols | Mol Fraction |
| Methanol | 0.9 | 32 | 0.027 | 0.01 |
| Dimethyl succinate | 62.5 | 146 | 0.428 | 0.14 |
| Monomethyl succinate | 284.3 | 132 | 2.154 | 0.70 |
| Succinic acid | 47.4 | 118 | 0.402 | 0.13 |
| Water | 0.9 | 18 | 0.048 | 0.02 |
| Total | 396.0 | | 3.060 | |

| Methanol Flow | | | | |
|---|---|---|---|---|
| Target (molar) | 4.0 | mol h$^{-1}$ mol$^{-1}$ (MMS) | 12.0 | mol MeOH h$^{-1}$ |
| Flow | 384.0 | g h$^{-1}$ | | |
| Density (Methanol) | 0.79 | g ml$^{-1}$ | | |
| Target Flow Rate | 8.10 | mL min$^{-1}$ | | |

TABLE 15

Results of Example 7 Run 2

| | Example 7 Run 2 | | | | | |
|---|---|---|---|---|---|---|
| Time, min | 0 | 16 | 25 | 35 | 46 | 59 |
| Mass Discharged (autoclave), g | 14.5 | 9.7 | 5.7 | 10.0 | 5.6 | 7.0 |
| Methnaol Flow Rate, ml min$^{-1}$ | 8.10 | 8.10 | 8.10 | 8.10 | 8.10 | 8.10 |
| Reaction Temperature, °C. | 188 | 184 | 183 | 186 | 187 | 187 |
| System Pressure, psig | | 168 | 170 | 164 | 164 | 163 |
| Autoclave Components | | | | | | |
| Methanol/GC, wt % | 1.097 | 12.053 | 12.823 | 11.526 | 12.693 | 12.709 |
| Dimethyl succinate/GC, wt % | 29.214 | 42.354 | 44.027 | 49.981 | 53.980 | 59.055 |
| Monomethyl succinate/GC, wt % | 48.730 | 34.006 | 32.199 | 27.850 | 25.688 | 22.081 |
| Succinic acid/GC, wt % | 18.440 | 6.156 | 5.372 | 3.860 | 2.948 | 2.209 |
| Water/KFT, wt % | 1.950 | 3.994 | 4.187 | 3.524 | 2.987 | 2.127 |
| Sum of Knowns, % | 99.4 | 98.6 | 98.6 | 96.7 | 98.3 | 98.2 |
| Conversion to Dimethyl succinate (C$_4$ Basis), % | 27.6 | 48.4 | 51.0 | 58.4 | 62.7 | 68.5 |
| Overheads Collected, g | 0.0 | 11.1 | 32.1 | 86.4 | 77.4 | 89.5 |
| Overheads, analysis | | | | | | |
| Methanol/GC, wt % | | 77.745 | 86.517 | 89.292 | 91.903 | 92.810 |
| Dimethyl succinate/GC, wt % | | 5.611 | 5.611 | 6.500 | 8.500 | 10.882 |
| Monomethyl succinate/GC, wt % | | 0.431 | 0.431 | 0.431 | 0.431 | 0.478 |
| Succinic acid/GC, wt % | | | 0.104 | | | 0.114 |
| Water/KFT, wt % | | 22.255 | 13.483 | 10.708 | 80.97 | 7.190 |
| Sums of Knowns | 0.0 | 106.0 | 106.1 | 106.9 | 108.9 | 111.5 |

TABLE 16

Results of Run 2 continued

| | Example 7 Run 2 (cont'd) Time, min | | | |
|---|---|---|---|---|
| | 73 | 90 | 105 | Final |
| Mass discharged (autoclave), g | 11.3 | 9.0 | 6.0 | 316.3 |
| Methanol Flow Rate, ml min$^{-1}$ | 8.10 | 8.10 | 8.10 | |
| Reaction Temperature, °C. | 187 | 187 | 187 | |
| System Pressure, psig | 160 | 154 | 162 | |
| Autoclave Components | | | | |
| Methanol/GC, wt % | 13.647 | 12.668 | 14.231 | 13.412 |
| Dimethyl succinate/GC, wt % | 64.972 | 68.887 | 70.613 | 75.011 |
| Monomethyl succinate/GC, wt % | 17.891 | 14.889 | 12.290 | 9.788 |
| Succinic acid/GC, wt % | 1.234 | 0.836 | 0.577 | 0.322 |
| Water/KFT, wt % | 1.265 | 0.795 | 0.537 | 0.529 |
| Sum of Knowns, % | 99.0 | 98.1 | 98.2 | 99.1 |
| Conversion to DMS (C$_4$ Basis), % | 75.3 | 79.7 | 83.2 | 87.0 |
| Overheads Collected, g | 103.9 | 126.8 | 103.8 | 19.6 |
| Overheads, analysis | | | | |
| MeOH/GC, wt % | 95.608 | 97.724 | 98.185 | 90.656 |
| Dimethyl succinate/GC, wt % | 11.500 | 12.399 | 13.399 | 16.000 |
| Monomethyl succinate/GC, wt % | 0.478 | 0.471 | 0.471 | 0.471 |
| Succinic acid/GC, wt % | | 0.142 | | |
| Water/KFT, wt % | 4.392 | 2.276 | 1.815 | 9.344 |
| Sum of Knowns | 112.0 | 113.0 | 113.9 | 116.5 |

EXAMPLE 8

This example demonstrates separation of di-methyl succinate from mono-methyl succinate by distillation under vacuum.

The expected stream composition from the bottom of an autocatalytic reaction column was made up artificially as feed using petrochemical dimethyl succinate, monomethyl succinate and succinic acid from previous experiments. The resulting composition in weight percents was:

| | |
|---|---|
| Methanol | 7.0 |
| Di-methyl Succinate | 63 |
| Mono-methyl Succinate | 27 |
| Succinic Acid | 2.9 |
| Others | 0.1 |

1032 g of this material was charged to an insulated 2 L round bottom flask, which heated by an isomantle acted as the reboiler for the batch distillation. The temperature of the isomantle was controlled using a Watlow burst fire module with a k type thermocouple attached to the skin of the vessel. A further k type thermocouple was located inside the reboiler to determine the actual process temperature.

The distillation was performed using a 1" diameter glass column containing twelve pieces of Sulzer type EX structured packing, operated in continuous mode. The column also had two zones heated by electrical heating tape enabling the temperature of both the top and bottom areas of the column to be controlled.

A Liebig condenser was used on the top of the column to cool/condense the overheads. The overheads were connected to a vacuum pump, with a target overheads pressure of 400 mbar to allow the separation to be performed at reduced reboiler temperature. Overheads were removed on a continuous basis, with the mass withdrawn measured periodically and compositional analysis performed. Overheads were analysed for water (HP08) and dimethyl succinate/methanol AS08 (30 m×0.32 mm DB-FFAP column), with the acid content (as mono-methyl succinate) determined by titration with 0.1N KOH using methanolic phenolphthalein indicator solution.

Analysis of the chemical composition of the reboiler was carried out by gas chromatography (GC) using N,O-bis trimethylsilylacetamide (Regisil) to allow the resolution of acidic species to be achieved. The level of methanol, dimethyl succinate, monomethyl succinate, and succinic acid were determined (Sil8 column 50 m×0.32 mm). Reboiler samples were also analysed for acid content by means of a base titration with 0.1N KOH using methanolic phenolphthalein indicator solution. Water analysis was performed on HP08 which as was fitted with a thermal conductivity detector (TCD).

The overheads and reboiler compositions measured, along with temperature and pressure data for this test are set out in Table 17.

TABLE 17

Results of Distillation of Dimethyl Succinate and Monomethyl Succinate At 400 mbar Pressure

| Time on Line (hours) | 0 | 0.25 | 0.75 | 1.75 | 3 |
|---|---|---|---|---|---|
| Temperatures | | | | | |
| Reboiler Skin (° C.) | | 196 | 210 | 225 | 224 |
| Reboiler Pot (° C.) | | 106 | 153 | 181 | 185 |
| Column Wall TWI (bottom) (° C.) | | 84.3 | 103.3 | 159.5 | 154 |
| Column Heater, TTI (bottom) (° C.) | | 92.3 | 82.7 | 177.9 | 164.4 |
| Column Wall TWI (top) (° C.) | | 21.8 | 34.9 | 110.9 | 117 |
| Column Heater, TTI (top) (° C.) | | 41.7 | 26 | 147.3 | 149.5 |
| Overheads (° C.) | | 37.6 | 28.8 | | 138.8 |
| Pressure (mbar) | | 490 | 399 | 374 | 429 |
| Pot Contents (g) | 1032 | 982.1 | 949.2 | 933.5 | 920.4 |
| Overheads Weight (g) | | 48.86 | 30.94 | 12.72 | 11.09 |
| Bottoms Sample Weight (g) | | 1 | 2 | 3 | 2 |
| Overheads Analysis | | | | | |
| Methanol wt % | | 86.42 | 27.11 | 2.067 | 0.375 |
| Dimethyl Succinate wt % | | 0.312 | 56.76 | 92.06 | 96.99 |
| Acid (as Monomethyl Succinate) wt % | | 0.537 | 0.038 | 0.11 | 0.147 |
| Water wt % | | 12.73 | 15.36 | 4.627 | 1.129 |
| Others wt % | | 0 | 0.736 | 1.1340 | 1.353 |
| Total | | 100 | 100 | 100 | 100 |
| Pot Analysis | | | | | |
| Methanol wt % | 7.00 | 0.27 | 0 | 0 | 0 |
| Dimethyl Succinate wt % | 63.00 | 65.73 | 65.99 | 65.71 | 66.19 |
| Monomethyl Succinate wt % | 27.00 | 29.68 | 29.25 | 29.86 | 30.08 |
| Succinic acid wt % | 2.90 | 3.43 | 2.80 | 2.07 | 1.176 |
| Water wt % | 0.00 | 0.88 | 1.76 | 1.63 | 0 |
| Succinic anhydride wt % | 0.00 | 0.00 | 0.19 | 0.72 | 0.589 |
| Others wt % | 0.10 | 0.00 | 0.00 | 0.00 | 2.554 |
| Total | 100.00 | 100.00 | 100.00 | 100.00 | 100.59 |

| Time on Line (hours) | 4 | 5 | 6 | 7 | 8 | 8.67 |
|---|---|---|---|---|---|---|
| Temperatures | | | | | | |
| Reboiler Skin (° C.) | 230 | 225 | 226 | 226 | 223 | 223 |
| Reboiler Pot (° C.) | 192 | 198 | 200 | 200 | 197 | 197 |
| Column Wall TWI (bottom) (° C.) | 159.5 | 158.7 | 158.6 | 158.2 | 159.2 | 159.2 |
| Column Heater, TTI (bottom) (° C.) | 161.8 | 153 | 157 | 164.5 | 159.6 | 159.6 |
| Column Wall TWI (top) (° C.) | 121.6 | 122.9 | 120.1 | 135.6 | 132.5 | 132.5 |
| Column Heater, TTI (top) (° C.) | 155.1 | 157.6 | 151 | 86 | 103.3 | 103.3 |
| Overheads (° C.) | 145.2 | 145.1 | 135.1 | 128.5 | 113.3 | 113.3 |
| Pressure (mbar) | 501 | 637 | 638 | 600 | 450 | 450 |
| Pot Contents (g) | 872.0 | 801.2 | 660.9 | 576.6 | 438.4 | 420.1 |

TABLE 17-continued

Results of Distillation of Dimethyl Succinate and Monomethyl Succinate At 400 mbar Pressure

| | | | | | | |
|---|---|---|---|---|---|---|
| Overheads Weight (g) | 46.38 | 68.86 | 138.3 | 82.22 | 136.2 | 16.35 |
| Bottoms Sample Weight (g) | 2 | 2 | 2 | 2 | 2 | 2 |
| Overheads Analysis | | | | | | |
| Methanol wt % | 0.199 | 0 | 0 | 0 | 0 | 0 |
| Dimethyl Succinate wt % | 98.36 | 98.61 | 99.08 | 94.36 | 99.22 | 98.99 |
| Acid (as Monomethyl Succinate) wt % | 0.01 | 0.006 | 0.01 | 4.933 | 0.17 | 0.1 |
| Water wt % | 0.288 | 0.164 | 0.074 | 0.104 | 0.056 | 0.084 |
| Others wt % | 1.147 | 1.218 | 0.839 | 0.608 | 0.559 | 0.828 |
| Total | 100 | 100 | 100 | 100 | 100 | 100 |
| Pot Analysis | | | | | | |
| Methanol wt % | 0 | 0 | 0 | 0 | 0 | 0 |
| Dimethyl Succinate wt % | 66.77 | 66.16 | 60.36 | 48.16 | 40.06 | 41.38 |
| Monomethyl Succinate wt % | 29.25 | 29.32 | 34.02 | 46.53 | 53.44 | 51.88 |
| Succinic acid wt % | 1.022 | 0.9683 | 1.190 | 2.113 | 2.623 | 3.411 |
| Water wt % | 0.0036 | 0.0667 | 0 | 0.1445 | 0 | 0 |
| Succinic anhydride wt % | 1.730 | 2.279 | 2.751 | 1.875 | 2.565 | 1.695 |
| Others wt % | 2.955 | 3.4855 | 4.428 | 3.056 | 3.880 | 3.319 |
| Total | 101.73 | 102.28 | 102.75 | 101.88 | 102.56 | 101.69 |

The invention claimed is:

1. A process for the production of dialkyl succinate from a bio-succinic acid feedstock comprising the steps of:
    (a) feeding solid bio-succinic acid to a first reactor where it is contacted with alkanol, said first reactor being operated at a suitable temperature and pressure to enable autocatalytic esterification to occur;
    (b) passing a stream removed from the first reactor comprising unreacted succinic acid, mono alkyl ester, dialkyl ester, alkanol, water and impurities to a point at or near the top of a reaction zone column operated at temperatures and pressures to enable esterification of the succinic acid and further esterification of the mono alkyl ester, and passing said stream in counter-current reaction to upflowing additional alkanol;
    (c) removing a stream from at or near the bottom of the reaction zone column comprising components selected from residual succinic acid, mono alkyl ester, dialkyl ester, impurities and alkanol and passing said stream to a bottoms stream separation zone where said di-alkyl ester is separated from alkanol, and from the succinic acid, mono alkyl ester and impurities;
    (d) recycling the succinic acid and mono alkyl ester to the reaction zone column;
    (e) removing at least some of the impurities as a purge; and
    (f) removing a stream comprising alkanol, water and organic components from at or near the top of the reaction zone column and passing said stream to a top stream distillation zone where the alkanol is separated, from the water and from the organic components and recycling the organic components to the reaction zone column.

2. The process according to claim 1 wherein said first reactor is a stirred tank reactor.

3. The process according to claim 2, wherein the stirred tank reactor is operated at a temperature in the region of from about 120° C. to about 140° C.

4. The process according to claim 2 wherein the pressure within the stirred tank reactor is in the region of from about 5 bara to about 10 bara.

5. The process according to claim 1 wherein the stream from the first reactor comprising unreacted succinic acid, mono alkyl ester, dialkyl ester, alkanol, water and impurities is passed via a subsequent reaction vessel.

6. The process according to claim 5 wherein the subsequent reaction vessel is a plug flow reaction vessel.

7. The process according to claim 1 wherein the stream is passed through a distillation column before being fed to the reaction zone column.

8. The process according to claim 1 wherein the reaction zone column is operated at an overhead pressure of about 1.3 bara to about 10 bara.

9. The process according to claim 1 wherein the reaction zone column is operated at a temperature of about 100° C. to about 300° C.

10. The process according to claim 1 wherein an alkanol wash is applied at or near the top of the reaction zone column.

11. The process according to claim 1 wherein the bottoms stream separation zone is a hydrogen stripping zone.

12. The process according to claim 1 wherein the bottoms stream separation zone is a bottom stream distillation zone.

13. The process according to claim 12 wherein the bottoms stream separation zone is operated at an overhead pressure of from about 0.1 bara to about 1 bara.

14. The process according to claim 12 wherein the dialkyl succinate is removed as a liquid side draw.

15. The process according to claim 14 wherein the liquid side draw is removed from a point above the feed point to the bottoms stream distillation zone.

16. The process according to claim 1 wherein the recovered alkanol from the bottoms stream separation zone is recycled to one or both of the first reactor and the reaction zone column.

17. The process according to claim 1 wherein the residual succinic acid and any mono-ester are recycled to the reaction zone column.

18. The process according to claim 17 wherein the recycled residual succinic acid any mono-ester are recycled to the reaction zone column at a point below the point at which the feed from the first reactor is added.

19. The process according to claim 1 wherein the impurities are removed as a purge from the bottoms stream separation zone.

20. The process according to claim 1 wherein the overhead from the reaction column zone comprising alkanol, water and organic components is passed to a condenser before being passed to a top stream distillation column.

21. The process according to claim 1 wherein the top stream distillation column is operated at an overhead pressure of about 1.3 bara to about 2 bara.

22. The process according to claim 1 wherein a liquid side draw is taken from the top stream distillation column.

23. The process according to claim 22 wherein the side draw is passed to a separator to separate an aqueous phase form an organic phase.

24. The process according to claim 23 wherein the organic phase is recycled to the reaction zone column.

25. The process according to claim 23 wherein the aqueous phase is returned to the top stream distillation column.

26. The process according to claim 25 wherein the aqueous phase is returned to the column at a point below the draw point for the liquid side draw.

27. The process according to claim 1 wherein the esterification in the reaction zone column and one or both of the distillation zones can be located in separate columns.

28. The process according to claim 1 wherein the alkanol is methanol.

* * * * *